US009651558B2

(12) United States Patent
Bosma

(10) Patent No.: US 9,651,558 B2
(45) Date of Patent: May 16, 2017

(54) BACTERIAL SURFACE DISPLAY AND SCREENING OF THIOETHER-BRIDGE-CONTAINING PEPTIDES

(75) Inventor: Tjibbe Bosma, Lippenhuizen (NL)

(73) Assignee: LanthioPep B.V., Groningen (NL)

(*) Notice: Subject to any disclaimer, the term of this patent is extended or adjusted under 35 U.S.C. 154(b) by 946 days.

(21) Appl. No.: 13/808,206

(22) PCT Filed: Jul. 6, 2011

(86) PCT No.: PCT/NL2011/050484
§ 371 (c)(1),
(2), (4) Date: Mar. 21, 2013

(87) PCT Pub. No.: WO2012/005578
PCT Pub. Date: Jan. 12, 2012

(65) Prior Publication Data
US 2013/0184177 A1     Jul. 18, 2013

(30) Foreign Application Priority Data

Jul. 6, 2010 (EP) .................................... 10168589

(51) Int. Cl.
    C12N 15/10      (2006.01)
    C12N 15/62      (2006.01)
    C12N 15/74      (2006.01)
    G01N 33/68      (2006.01)

(52) U.S. Cl.
    CPC ..... *G01N 33/6803* (2013.01); *C12N 15/1037* (2013.01); *C12N 15/625* (2013.01); *C07K 2319/035* (2013.01); *C07K 2319/50* (2013.01)

(58) Field of Classification Search
    None
    See application file for complete search history.

(56) References Cited

U.S. PATENT DOCUMENTS

| 7,238,489 B2 | 7/2007 | Schneewind | |
| 2010/0129341 A1* | 5/2010 | Sakon | A61K 38/29 424/94.6 |
| 2010/0143967 A1* | 6/2010 | McFarland | C12P 7/06 435/41 |

FOREIGN PATENT DOCUMENTS

| WO | 2005012491 A2 | 2/2005 |
| WO | WO 2006/062398 | 6/2006 |

OTHER PUBLICATIONS

Benhar, Biotch. Adv. 19:1-33, 2001.*
Ping Chen et al., Effect of amino acid substitutions in conserved residues in the leader peptide on biosynthesis of the lantibiotic mutacin II, FEMS Microbiology Letters 195 (2001) 139-144.
Hans-Georg Sahl et al., Lantibiotics: Biosynthesis and Biological Activities of Uniquely Modified Peptides from Gram-Positive Bacteria, Annu. Rev. Microbiol. (1998) 52:41-79.
Jan Roelof Van Der Meer, et al., Influence of Amino Acid Substitutions in the Nisin LEader Peptide on Biosynthesis and Secretion of Nisin by Lactococcus lactis*, The Journal of Biological Chemistry, (1994) vol. 269, No. 5 pp. 3555-3562.
Mingqiang Qiao, et al., Evidence for a role of NisT in transport of the lantibiotic nisin produced by Lactococcus lactis N8, FEMS Microbiology Letters, 144 (1996) 89-93.
Peter Kiesau, et al., Evidence for a Multimeric Subtilin Synthetase Complex, Journal of Bacteriology, (1997) vol. 179, No. 5 pp. 1475-1481.
Amit K. Galande, et al., Understanding Base-Assisted Desulfurization Using a Variety of Disulfide-Bridged Peptides, Biopolymners (Peptide Science), vol. 71, 534-551 (2003).
Katja Siegers, et al., Biosynthesis of Lantibiotic Nisin, The Journal of Biological Chemistry, vol. 271, No. 21, (1996) pp. 12294-12301.
Annechien Plat, et al., Requirements of the Engineered Leader Peptide of Nisin for Inducing Modification, Export, and Cleavage, Applied and Environmental Microbiology, Jan. 2011, p. 604-611.
Rick Rink, et al., Production of Dehydroamino Acid-Containing Peptides by Lactococcus lactis, Applied and Environmental Microbiology, Mar. 2007, vol. 73, No. 6, p. 1792-1796.
Bo Li, et al., Catalytic promiscuity in the biosynthesis of cyclic peptide secondary metabolites in planktonic marine cyanobacteria, PNAS (2010) vol. 107, No. 23 p. 10430-10435.
Roland J. Siezen, Multi-domain, cell-envelope proteinases of lactic acid bacteria, Antonie van Leeuwenhoek, vol. 76, p. 139-155 (1999).
William Wiley Navarre, et al., Surface Proteins of Gram-Positive Bacteria and Mechanisms of their Targeting to the Cell Wall Envelope, Microbiology and Molecular Biology Reviews, Mar. 1999, p. 174-229, vol. 63, No. 1.
Asuman Karakas Sen, et al., Post-translation modification of nisin, Eur. J. Biochem., 261, p. 524-532 (1999).
Luciano A. Marraffini, et al., Sortases and the Art of Anchoring Proteins to the Envelopes of Gram-Positive Bacteria, Microbiology and Molecular Biology Reviews, vol. 70, No. 1, p. 192-221(2006).
Kees Leenhouts, et al., Anchoring of proteins to lactic acid bacteria, XP-002493781, 76:367-376 (1999).
Anneke Kuiperst, et al., NisT, the Transporter of the Lantibiotic Nisin, Can Transport Fully Modified, Dehydrated, and Unmodified Prenisin and Fusions of the Leader Peptide with Non-lantibiotic Peptides, The Journal of Biological Chemistry, XP-002424517, vol. 279, No. 21 (2004) p. 22176-22182.
R. Rink, et al., To protect peptide pharmaceuticals against peptidases, Journal of Pharmacological and Toxicological Methods, XP-002601695 (2010) p. 210-218.

(Continued)

*Primary Examiner* — Nancy Treptow
(74) *Attorney, Agent, or Firm* — Licata & Tyrrell P.C.

(57) ABSTRACT

The invention relates to bacterial cell surface display of post-translationally modified heterologous proteins. Provided is an isolated nucleic acid construct encoding a proteinaceous substance comprising, from the N-terminus to the C-terminus, at least (a) an N-terminal a lantibiotic leader sequence; (b) an amino acid sequence of interest to be post-translationally modified to a dehydroresidue- or thioether-bridge containing polypeptide; (c) a hydrophilic cell-wall spanning domain; (d) a sortase recognition motif; (e) a hydrophobic membrane spanning domain and (f) a C-terminal charged membrane anchoring domain. Also provided is a Gram-positive host cell expressing the construct, as well as a library of host cells.

20 Claims, 11 Drawing Sheets

(56) References Cited

OTHER PUBLICATIONS

Figure 1A:
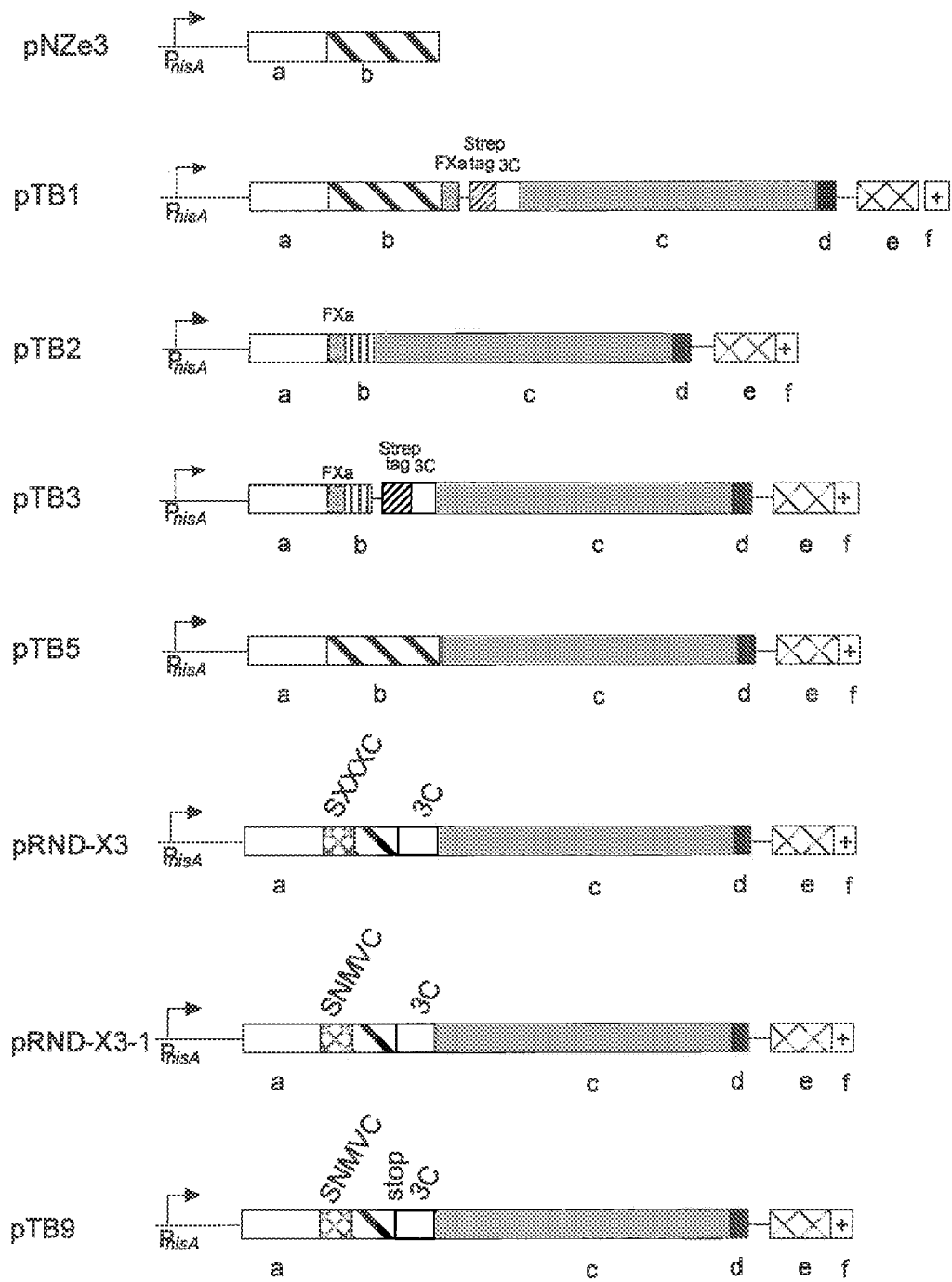

Gert N. Moll, et al., Microbial engineering of dehydro-amino acids and lanthionines in non-lantibiotic peptides, XP-002601694, Springer Science+Business Media B.V. (2010) 97:319-333.
Tjibbe Bosma, et al., Bacterial Display and Screening of Post-translationally Thioether-Stabilized Peptides, XP009153580, Applied and Environmental Microbiology, (2011) p. 6794-6831.
J. Lubelski, et al., Biosynthesis, immunity, regulation, mode of action and engineering of the model lantibiotic nisin, Cell. Mil. Life Sci. 65 (2008) 455-476.
G.N. Moll, et al., A biological stabilization technology for peptide drugs: enzymatic introduction of thioether-bridges, Drug Discovery Today: Technologies, XP-27503974, vol. 6 (2009).
Harold Tjalsma, et al., Signal Peptide-Dependent Protein Transport in Bacillus subtilis: a Genome-Based Survey of the Secretome, Microbiology and Molecular Biology Reviews, XP-002227136 (2000), p. 515-547.
Sen, et al., Post-translation modification of nisin, EUJ. Biochem., 261, p. 524-532 (1999).
Qiao et al, 1996. FEMS, Microbiol. Letter 144, 89-93.
Chen P., et al., Microbiol. Letter 2001; 195(2):139.
Neis, et al. FEMS Microbil. Letter 1997; 149(2):249.

\* cited by examiner

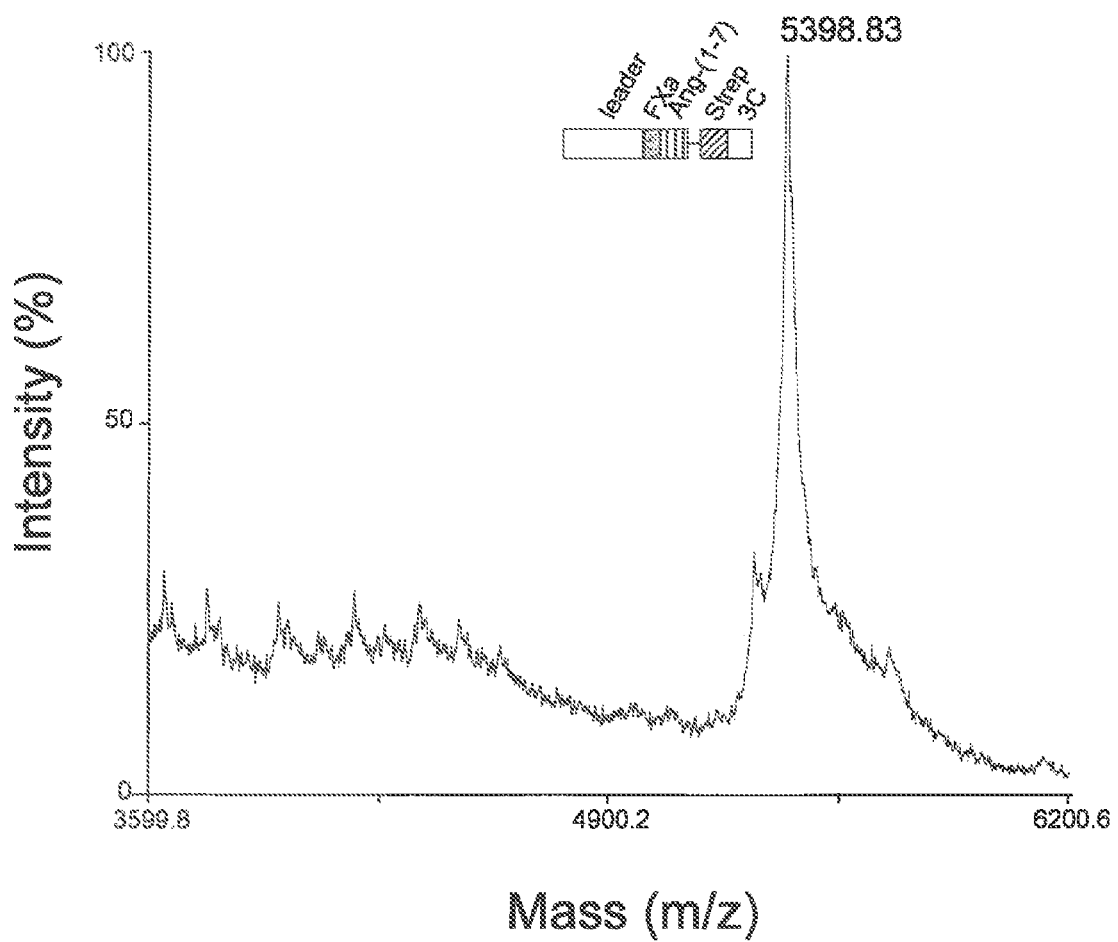

control peptide : LMRTTSSLELSDYEQAC (1948.17)

without CDAP with CDAP

TB3 without CDAP with CDAP no CDAP

CDAP

```
                         SEQUENCE LISTING

<160> NUMBER OF SEQ ID NOS: 30

<210> SEQ ID NO 1
<211> LENGTH: 10
<212> TYPE: PRT
<213> ORGANISM: Artificial
<220> FEATURE:
<223> OTHER INFORMATION: consensus sequence leader peptide
<220> FEATURE:
<221> NAME/KEY: MISC_FEATURE
<222> LOCATION: (1)..(1)
<223> OTHER INFORMATION: any hydrophobic amino acid
<220> FEATURE:
<221> NAME/KEY: VARIANT
<222> LOCATION: (2)..(2)
<223> OTHER INFORMATION: may be E
<220> FEATURE:
<221> NAME/KEY: VARIANT
<222> LOCATION: (4)..(4)
<223> OTHER INFORMATION: may be L
<220> FEATURE:
<221> NAME/KEY: VARIANT
<222> LOCATION: (5)..(5)
<223> OTHER INFORMATION: may be T
<220> FEATURE:
<221> NAME/KEY: VARIANT
<222> LOCATION: (6)..(6)
<223> OTHER INFORMATION: may be E
<220> FEATURE:
<221> NAME/KEY: MISC_FEATURE
<222> LOCATION: (7)..(7)
<223> OTHER INFORMATION: any hydrophobic amino acid
<220> FEATURE:
<221> NAME/KEY: VARIANT
<222> LOCATION: (10)..(10)
```

```
<223> OTHER INFORMATION: may be E

<400> SEQUENCE: 1

Xaa Asp Glu Val Ser Asp Xaa Glu Leu Asp
1               5                   10

<210> SEQ ID NO 2
<211> LENGTH: 10
<212> TYPE: PRT
<213> ORGANISM: Artificial
<220> FEATURE:
<223> OTHER INFORMATION: leader peptide sequence

<400> SEQUENCE: 2

Leu Glu Glu Val Ser Glu Gln Glu Leu Asp
1               5                   10

<210> SEQ ID NO 3
<211> LENGTH: 5
<212> TYPE: PRT
<213> ORGANISM: Artificial
<220> FEATURE:
<223> OTHER INFORMATION: leader peptide consensus sequence
<220> FEATURE:
<221> NAME/KEY: VARIANT
<222> LOCATION: (2)..(2)
<223> OTHER INFORMATION: may be E or N
<220> FEATURE:
<221> NAME/KEY: VARIANT
<222> LOCATION: (4)..(4)
<223> OTHER INFORMATION: may be E or N
<220> FEATURE:
<221> NAME/KEY: VARIANT
<222> LOCATION: (5)..(5)
<223> OTHER INFORMATION: may be I or V

<400> SEQUENCE: 3

Phe Asp Leu Asp Leu
1               5

<210> SEQ ID NO 4
<211> LENGTH: 6
<212> TYPE: PRT
<213> ORGANISM: Artificial
<220> FEATURE:
<223> OTHER INFORMATION: leader peptide

<400> SEQUENCE: 4

Leu Phe Asp Leu Asp Leu
1               5

<210> SEQ ID NO 5
<211> LENGTH: 5
<212> TYPE: PRT
<213> ORGANISM: Artificial
<220> FEATURE:
<223> OTHER INFORMATION: leader peptide

<400> SEQUENCE: 5

Phe Asn Leu Asp Val
1               5

<210> SEQ ID NO 6
<211> LENGTH: 8
<212> TYPE: PRT
<213> ORGANISM: Artificial
<220> FEATURE:
<223> OTHER INFORMATION: leader peptide consensus sequence
<220> FEATURE:
```

```
<221> NAME/KEY: VARIANT
<222> LOCATION: (1)..(1)
<223> OTHER INFORMATION: may be L
<220> FEATURE:
<221> NAME/KEY: VARIANT
<222> LOCATION: (2)..(2)
<223> OTHER INFORMATION: may be F
<220> FEATURE:
<221> NAME/KEY: VARIANT
<222> LOCATION: (3)..(3)
<223> OTHER INFORMATION: may be E or N
<220> FEATURE:
<221> NAME/KEY: VARIANT
<222> LOCATION: (6)..(6)
<223> OTHER INFORMATION: may be N, A, S or T
<220> FEATURE:
<221> NAME/KEY: VARIANT
<222> LOCATION: (7)..(7)
<223> OTHER INFORMATION: may be M
<220> FEATURE:
<221> NAME/KEY: VARIANT
<222> LOCATION: (8)..(8)
<223> OTHER INFORMATION: may be E

<400> SEQUENCE: 6

Ile Leu Asp Leu Gln Asp Leu Asp
1               5

<210> SEQ ID NO 7
<211> LENGTH: 8
<212> TYPE: PRT
<213> ORGANISM: Artificial
<220> FEATURE:
<223> OTHER INFORMATION: leader peptide

<400> SEQUENCE: 7

Ile Leu Glu Leu Gln Asn Leu Asp
1               5

<210> SEQ ID NO 8
<211> LENGTH: 4
<212> TYPE: PRT
<213> ORGANISM: Artificial
<220> FEATURE:
<223> OTHER INFORMATION: membrane spanning domain

<400> SEQUENCE: 8

Pro Ala Phe Gly
1

<210> SEQ ID NO 9
<211> LENGTH: 4
<212> TYPE: PRT
<213> ORGANISM: Artificial
<220> FEATURE:
<223> OTHER INFORMATION: membrane spanning domain

<400> SEQUENCE: 9

Phe Gly Phe Leu
1

<210> SEQ ID NO 10
<211> LENGTH: 5
<212> TYPE: PRT
<213> ORGANISM: Artificial
<220> FEATURE:
<223> OTHER INFORMATION: membrane spanning domain

<400> SEQUENCE: 10

Leu Gly Val Ile Val
```

```
<210> SEQ ID NO 11
<211> LENGTH: 6
<212> TYPE: PRT
<213> ORGANISM: Artificial
<220> FEATURE:
<223> OTHER INFORMATION: membrane spanning domain

<400> SEQUENCE: 11

Val Ile Val Val Ile Leu
1               5

<210> SEQ ID NO 12
<211> LENGTH: 5
<212> TYPE: PRT
<213> ORGANISM: Artificial
<220> FEATURE:
<223> OTHER INFORMATION: membrane spanning domain

<400> SEQUENCE: 12

Ile Leu Met Gly Val
1               5

<210> SEQ ID NO 13
<211> LENGTH: 5
<212> TYPE: PRT
<213> ORGANISM: Artificial
<220> FEATURE:
<223> OTHER INFORMATION: membrane spanning domain

<400> SEQUENCE: 13

Gly Val Leu Gly Leu
1               5

<210> SEQ ID NO 14
<211> LENGTH: 19
<212> TYPE: PRT
<213> ORGANISM: Artificial
<220> FEATURE:
<223> OTHER INFORMATION: membrane spanning domain

<400> SEQUENCE: 14

Pro Ala Phe Gly Phe Leu Gly Val Ile Val Val Ile Leu Met Gly Val
1               5                   10                  15

Leu Gly Leu

<210> SEQ ID NO 15
<211> LENGTH: 5
<212> TYPE: PRT
<213> ORGANISM: Artificial
<220> FEATURE:
<223> OTHER INFORMATION: LPXTG motif
<220> FEATURE:
<221> NAME/KEY: VARIANT
<222> LOCATION: (3)..(3)
<223> OTHER INFORMATION: may be D, E, A, N or Q

<400> SEQUENCE: 15

Leu Pro Lys Thr Gly
1               5

<210> SEQ ID NO 16
<211> LENGTH: 7
<212> TYPE: PRT
<213> ORGANISM: Artificial
<220> FEATURE:
```

```
<223> OTHER INFORMATION: C-terminus

<400> SEQUENCE: 16

Lys Arg Lys Gln Arg Glu Glu
1               5

<210> SEQ ID NO 17
<211> LENGTH: 4
<212> TYPE: PRT
<213> ORGANISM: Artificial
<220> FEATURE:
<223> OTHER INFORMATION: factor Xa protease recognition site

<400> SEQUENCE: 17

Ile Glu Gly Arg
1

<210> SEQ ID NO 18
<211> LENGTH: 23
<212> TYPE: PRT
<213> ORGANISM: Artificial
<220> FEATURE:
<223> OTHER INFORMATION: nisin leaderpeptide

<400> SEQUENCE: 18

Met Ser Thr Lys Asp Phe Asn Leu Asp Leu Val Ser Val Ser Lys Lys
1               5                   10                  15

Asp Ser Gly Ala Ser Pro Arg
            20

<210> SEQ ID NO 19
<211> LENGTH: 21
<212> TYPE: PRT
<213> ORGANISM: Artificial
<220> FEATURE:
<223> OTHER INFORMATION: modifiable peptide

<400> SEQUENCE: 19

Ile Ser Asn Met Val Cys Asn Met Lys Thr Ala Thr Cys His Cys Ser
1               5                   10                  15

Ile His Val Ser Lys
            20

<210> SEQ ID NO 20
<211> LENGTH: 186
<212> TYPE: PRT
<213> ORGANISM: Artificial
<220> FEATURE:
<223> OTHER INFORMATION: membrane anchor protein

<400> SEQUENCE: 20

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys Ile Glu Gly Arg Gly Gln Ser
    50                  55                  60

Leu Lys Thr Lys Val Ala Ala Val Glu Ala Lys Thr Val
65                  70                  75                  80

Lys Gly Asp Gly Thr Thr Gly Thr Ser Asp Lys Gly Gly Gln Gly
                85                  90                  95
```

Thr Pro Ala Pro Ala Pro Gly Asp Ile Gly Lys Asp Lys Gly Asp Glu
            100                 105                 110

Gly Ser Gln Pro Ser Ser Gly Gly Asn Ile Pro Thr Asn Pro Ala Thr
            115                 120                 125

Thr Thr Ser Thr Ser Thr Asp Asp Thr Thr Asp Arg Asn Gly Gln Leu
            130                 135                 140

Thr Ser Gly Lys Gly Ala Leu Pro Lys Thr Gly Glu Thr Thr Glu Arg
145                 150                 155                 160

Pro Ala Phe Gly Phe Leu Gly Val Ile Val Val Ile Leu Met Gly Val
                165                 170                 175

Leu Gly Leu Lys Arg Lys Gln Arg Glu Glu
            180                 185

<210> SEQ ID NO 21
<211> LENGTH: 179
<212> TYPE: PRT
<213> ORGANISM: Artificial
<220> FEATURE:
<223> OTHER INFORMATION: truncated membrane anchor protein

<400> SEQUENCE: 21

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
            35                  40                  45

Cys His Cys Ser Ile His Val Ser Lys Ile Glu Gly Arg Gly Gln Ser
    50                  55                  60

Leu Lys Thr Lys Val Ala Ala Val Glu Ala Ala Lys Thr Val Gly
65                  70                  75                  80

Lys Gly Asp Gly Thr Thr Gly Thr Ser Asp Lys Gly Gly Gln Gly
                85                  90                  95

Thr Pro Ala Pro Ala Pro Gly Asp Ile Gly Lys Asp Lys Gly Asp Glu
            100                 105                 110

Gly Ser Gln Pro Ser Ser Gly Gly Asn Ile Pro Thr Asn Pro Ala Thr
            115                 120                 125

Thr Thr Ser Thr Ser Thr Asp Asp Thr Thr Asp Arg Asn Gly Gln Leu
            130                 135                 140

Thr Ser Gly Lys Gly Ala Leu Pro Lys Thr Gly Glu Thr Thr Glu Arg
145                 150                 155                 160

Pro Ala Phe Gly Phe Leu Gly Val Ile Val Val Ile Leu Met Gly Val
                165                 170                 175

Leu Gly Leu

<210> SEQ ID NO 22
<211> LENGTH: 150
<212> TYPE: PRT
<213> ORGANISM: Artificial
<220> FEATURE:
<223> OTHER INFORMATION: truncated membrane anchor protein

<400> SEQUENCE: 22

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

```
Gly Cys Lys Thr Gly Ala Leu Met Gly Cys Asn Met Lys Thr Ala Thr
            35                  40                  45

Cys His Cys Ser Ile His Val Ser Lys Ile Glu Gly Arg Gly Gln Ser
    50                  55                  60

Leu Lys Thr Lys Val Ala Ala Val Glu Ala Ala Lys Thr Val Gly
65                  70                  75                  80

Lys Gly Asp Gly Thr Thr Gly Thr Ser Asp Lys Gly Gly Gln Gly
                85                  90                  95

Thr Pro Ala Pro Ala Pro Gly Asp Ile Gly Lys Asp Lys Gly Asp Glu
            100                 105                 110

Gly Ser Gln Pro Ser Ser Gly Gly Asn Ile Pro Thr Asn Pro Ala Thr
            115                 120                 125

Thr Thr Ser Thr Ser Thr Asp Asp Thr Thr Asp Arg Asn Gly Gln Leu
            130                 135                 140

Thr Ser Gly Lys Gly Ala
145                 150
```

```
<210> SEQ ID NO 23
<211> LENGTH: 105
<212> TYPE: PRT
<213> ORGANISM: Artificial
<220> FEATURE:
<223> OTHER INFORMATION: truncated membrane anchor protein

<400> SEQUENCE: 23

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
            35                  40                  45

Cys His Cys Ser Ile His Val Ser Lys Ile Glu Gly Arg Gly Gln Ser
    50                  55                  60

Leu Lys Thr Lys Val Ala Ala Val Glu Ala Ala Lys Thr Val Gly
65                  70                  75                  80

Lys Gly Asp Gly Thr Thr Gly Thr Ser Asp Lys Gly Gly Gln Gly
                85                  90                  95

Thr Pro Ala Pro Ala Pro Gly Asp Ile
            100                 105
```

```
<210> SEQ ID NO 24
<211> LENGTH: 85
<212> TYPE: PRT
<213> ORGANISM: Artificial
<220> FEATURE:
<223> OTHER INFORMATION: truncated membrane anchor protein

<400> SEQUENCE: 24

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
            35                  40                  45

Cys His Cys Ser Ile His Val Ser Lys Ile Glu Gly Arg Gly Gln Ser
    50                  55                  60

Leu Lys Thr Lys Val Ala Ala Ala Val Glu Ala Ala Lys Thr Val Gly
```

```
                65                  70                  75                  80

Lys Gly Asp Gly Thr
                85

<210> SEQ ID NO 25
<211> LENGTH: 7
<212> TYPE: PRT
<213> ORGANISM: Artificial
<220> FEATURE:
<223> OTHER INFORMATION: angiotensin 1-7

<400> SEQUENCE: 25

Asp Arg Val Ser His Ile Cys
1               5

<210> SEQ ID NO 26
<211> LENGTH: 21
<212> TYPE: PRT
<213> ORGANISM: Artificial
<220> FEATURE:
<223> OTHER INFORMATION: library streptavidin binding peptide
<220> FEATURE:
<221> NAME/KEY: MISC_FEATURE
<222> LOCATION: (3)..(4)
<223> OTHER INFORMATION: may be any amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 26

Ile Ser Xaa Xaa Xaa Cys Asn Met Lys Thr Ala Thr Cys His Cys Ser
1               5                   10                  15

Ile His Val Ser Lys
            20

<210> SEQ ID NO 27
<211> LENGTH: 5
<212> TYPE: PRT
<213> ORGANISM: Artificial
<220> FEATURE:
<223> OTHER INFORMATION: sortase recoginition motif
<220> FEATURE:
<221> NAME/KEY: VARIANT
<222> LOCATION: (3)..(3)
<223> OTHER INFORMATION: may be D, E, A, N or Q

<400> SEQUENCE: 27

Leu Pro Lys Thr Gly
1               5

<210> SEQ ID NO 28
<211> LENGTH: 7
<212> TYPE: PRT
<213> ORGANISM: Artificial
<220> FEATURE:
<223> OTHER INFORMATION: human rhinovirus 3C protease recognition site

<400> SEQUENCE: 28

Glu Ala Leu Phe Gln Gly Pro
1               5

<210> SEQ ID NO 29
<211> LENGTH: 17
<212> TYPE: PRT
<213> ORGANISM: Artificial
<220> FEATURE:
<223> OTHER INFORMATION: control peptide
```

-continued

```
<400> SEQUENCE: 29

Leu Met Arg Thr Thr Ser Ser Leu Glu Leu Ser Asp Tyr Glu Gln Ala
1               5                   10                  15

Cys

<210> SEQ ID NO 30
<211> LENGTH: 49
<212> TYPE: PRT
<213> ORGANISM: Artificial
<220> FEATURE:
<223> OTHER INFORMATION: thioether-bridged angiotensin anchor fusion
      peptide TB3 fragment

<400> SEQUENCE: 30

Ser Thr Lys Asp Phe Asn Leu Asp Leu Val Ser Val Ser Lys Lys Asp
1               5                   10                  15

Ser Gly Ala Ser Pro Arg Ile Glu Gly Arg Asp Arg Val Ser Ile His
            20                  25                  30

Cys Gly Gly Gly Trp Ser His Pro Gln Phe Glu Lys Glu Ala Leu Phe
        35                  40                  45

Gln
```

BACTERIAL SURFACE DISPLAY AND SCREENING OF THIOETHER-BRIDGE-CONTAINING PEPTIDES

This application is the U.S. National Phase of, and Applicants claim priority from, International Application No. PCT/NL2011/050484 filed Jul. 6, 2011 and European Patent Application No. 10168589.9 filed Jul. 6, 2010, each of which are incorporated herein by reference.

BACKGROUND OF THE INVENTION

The invention relates to the field of protein engineering and screening for therapeutically relevant peptide. More specifically, it relates to cell surface display of post-translationally modified heterologous proteins. Heterologous display of proteins or peptides on the surface of a microorganism (e.g. bacteria) is a useful research tool and has been associated with a broad range of interesting applications. Linking the protein or peptide function to the encoding gene enables the selection and/or optimization of peptides with desired properties from large combinatorial libraries. Various display formats have been developed including, ribosome display, phage display, bacterial surface display, and yeast display. Phage display is probably the best known system.

One of the most interesting applications of cell surface display is the selection of high affinity ligands from large libraries to therapeutically interesting target molecules. Thus far, only linear peptides, disulfide-linked cyclic peptides, and peptides coupled to an organic core have been displayed. This has resulted in the identification of various useful peptides, including therapeutically effective (lead) peptides. However, the proteolytic susceptibility and instability of these peptides has been recognized as a major disadvantage for therapeutic applications. The post-translational introduction of a cyclic structure in peptides, for instance a thioether crosslink, could circumvent these stability problems. However, at present it is still difficult to efficiently introduce such structures into synthetic peptides, especially for large peptides.

DESCRIPTION OF THE INVENTION

The present inventors aimed at providing a novel display system that allows for cell surface display of dehydroamino acid and or thioether-containing peptides. To that end, a unique recombinant nucleic acid construct was constructed which encodes a fusion peptide comprising, in addition to the peptide sequence to be cyclised, a combination of specific functional elements. It was surprisingly found that cyclic structures could readily be produced by, and displayed on, the surface of a host cell expressing the construct and comprising the biosynthetic and export machinery for lantibiotics, such as *L. lactis*. More specifically, the invention provides an isolated nucleic acid sequence encoding a fusion peptide comprising, from the N-terminus to the C-terminus, at least the following elements:
 (a) an N-terminal lantibiotic leader sequence
 (b) an amino acid sequence of interest to be post-translationally modified to a dehydroresidue- or thioether-containing polypeptide
 (c) a hydrophilic cell-wall spanning domain
 (d) a sortase recognition motif
 (e) a hydrophobic membrane spanning domain
 (f) a C-terminal charged membrane anchoring domain.

Other aspects of the invention relate to an expression vector comprising the isolated nucleic acid, a host cell comprising the expression vector and a library of host cells comprising a plurality of host cells. The invention is also applicable to produce (a library of) host cells expressing dehydroresidue-containing peptides.

The specific nucleic acid construct allows to exploit a bacterial host system both for the post-translational enzymatic modification of the encoded peptide as well as for display of the modified (cyclised) peptide. Other display systems known in the art such as phage display may in theory be suitable to express and display peptides that can be cyclised by chemical means, for example base-assisted desulfurization of disulfide bridged peptides (Galande et al. 2003 Biopolymers 71, 534-551). However, it was observed that the alkaline conditions strongly reduce phage viability and infectivity. In contrast, the present invention allows to use highly robust Gram-positive host cells, in particular lactic acid bacteria, which can withstand harsh conditions e.g. during screening. Furthermore, ring closure by chemical means is not stereo- and regiospecific; a given peptide with two L-Cys residues forming a disulfide bridge would yield a mixture of three diastereomeric lanthionine-containing peptides, the configuration of lanthionines being LL, LD, and DL. In contrast, the lanthinione enzyme machinery solely yields DL-stereoisomers and in the case of multiple rings only one ring pattern. Furthermore no execution of cost-rising reaction steps with undefined yield is required; the modification and display all being intrinsic to the bacterial system. Still further, the size of (lactic acid) bacteria is large enough to use FACS analysis for screening.

Lantibiotic-synthesizing enzymes have been described as being organized in a membrane-bound complex (Siegers et al. 1996. J. Biol. Chem. 271, 12294-12301; Kiesau et al. 1997. J. Bacteriol. 179, 1475-1481; Sahl et al. 1998. Annu. Rev. Microbiol. 52:41-7). This complex is composed of the lantibiotic transporter (LanT), the dehydrating enzyme (LanB; also referred to as dehydratase) and the cyclase (LanC). In the case of some lantibiotics a bifunctional enzyme (LanM) performs both the dehydration and the cyclization steps. The N-terminal lantibiotic leader peptide in the ribosomally synthesized prepropeptides is a recognition signal for the lantibiotic enzymes, starting with the dehydrating enzyme or the enzyme which performs both dehydration and ring formation. It is thought that the leader peptide binds to the lantibiotic complex to bring the prepropeptide in close proximity of the lantibiotic enzymes. The enzyme complexes suggest that it is necessary that the dehydrating and ring forming enzymes are attached to the transporter because a lantibiotic prepropeptide would otherwise be exported without undergoing modification or, alternatively, a modified peptide would accumulate in the cell.

In most cases, translocation of the lantibiotic depends entirely on the dedicated lantibiotic transporter. Disruption of the nisin transporter (NisT) was shown to cause accumulation of fully modified prenisin inside the cells (Qiao et al. 1996. FEMS Microbiol. Lett. 144, 89-93). Kuipers et al. previously showed that the lantibiotic transporter NisT can excrete unmodified lantibiotics and fusions of the leader peptide with non-lantibiotic peptides and that the combination of a dehydrating enzyme and the lantibiotic transporter, in the absence of the cyclase, is also functional (2004. J. Biol. Chem. 279, 22176-22182).

The above specific combination and relative order of the six different elements in a single fusion protein is not known or derivable from the prior art.

WO2006/062398 in the name of the applicant discloses several lantibiotic leader peptides and their uses, e.g. in fusion proteins to produce a peptide of interest which is to be post-translationally dehydrated by a dehydratase. According to WO2006/062398, the leader peptide and peptide to be modified are preceded by a non-lantibiotic export signal, like the SEC export signal. The export signal and leader peptide may be separated by a cell anchor sequence, for instance an LPTX-sortase recognition motif. WO2006/062398 fails to disclose elements (c), (e) and (f).

Moll et al. Antonie van Leeuwenhoed Vol. 97. No. 4, 2010, pp. 319-333 is a review on microbial engineering of dehydro-amino acids and lanthionines in non-lantibiotic peptides. It generally teaches that microbial engineering of lanthionines in peptides may allow the generation of unique libraries and concomitant display systems. Nothing is mentioned on how such libraries of lanthionine-containing peptides can be technically achieved, let alone that it suggests the unique approach of the present invention which involves the display of peptides with a post-translationally introduced ring structure. Rather, the skilled person would have opted for a more routine approach, like phage display of disulphide-containing peptides followed by chemical ring closure.

Rink et al. (2010) J. of Pharmac. And Toxic. Methods, Vol. 61, No. 2 pp. 210-218 relates to the stabilization of pharmaceutical peptides by introduction of D-amino acids and cyclization. A peptide of interest is directly or via a spacer genetically fused to a lantibiotic leader peptide. Nothing is mentioned about cell surface display of post-translationally cyclized peptides.

Leenhouts et al. (1999) Antonie van Leeuwenhoek, Vol. 76, No. 1-4, pp. 367-376 discloses several methods to anchor protein to the cell wall, including the LPXTG anchor motif. It also teaches that a charged tail and hydrophobic domains can act as a temporary stop to position the anchor motif for proteolytic cleavage. As in WO2006/062398, the elements are discussed in combination with the Sec signal sequence and SEC-mediated export. Leenhouts is silent about the combination of any anchoring motif with an element to be recognized by the lantibiotic machinery.

Any type of lantibiotic leader sequence can be used for practising the present invention, provided that it can be recognized by at least a lantibiotic dehydratase, and preferably also by a cyclase that can form a lanthionine-bridge. In one embodiment, a leader peptide in a polypeptide of the invention bears a lantibiotic leader consensus motif that can be derived from the amino acid sequence alignment of known lantibiotic leader peptides. Amino acid sequences of lantibiotic leader peptides are available from public databases. For example, Tables 1A and 1B of WO2006/062398 in the name of the applicant, show exemplary alignments of lantibiotic leader peptides. A skilled person will be able to derive a consensus motif from the aligned sequences, for instance using publicly or commercially available alignment software such as AlignX of Vector NTI. AlignX performs multiple sequence alignments on both protein and nucleic acid sequences uses using the ClustalW algorithm. It plots homology, sequence complexity, phylogenetic trees, and dot-matrix homology plots. AlignX accepts standard, feature-rich, text files of sequence, such as GenBank, EMBL and GenPept files. On one embodiment, the consensus motif is derived from the sequences in Table 1 using the ClustalW algorithm. It is preferred that a leader peptide consensus motif is derived from an alignment of at least 5, more preferably at least 10, most preferably at least 15 known leader peptide sequences. The thus obtained consensus motif can subsequently be verified for leader peptide activity, i.e. recognition by a lantibiotic dehydratase and serine or threonine dehydration, using methods known in the art. Dehydration of a given target sequence, e.g. ITSISRASVA, can be monitored using Maldi-TOF MS.

The leader peptide consensus sequence can comprise various consensus sequences, for instance the consensus motif X1-D/E-E-V/L-S/T-D/E-X2-E-L-D/E, wherein X1 is any hydrophobic amino acid and wherein X2 is any amino acid. For example, it comprises the sequence LEEVSE-QELD. In another embodiment, a leader peptide comprises a consensus motif F-D/E/N-L-D/E/N-X3, wherein X3 is L, I or V. For example, it comprises the sequence LFDLDL or FNLDV. The leader may for instance also contain the consensus I/L-L/F-D/E/N-L-Q-D/N/A/S/T-L/M-D/E comprising ILELQNLD. The leader peptide may be composed of the consensus sequence e.g. FNLDV followed by a spacer sequence between the consensus sequence and the modifable propeptide. This spacer sequence is required to bring the modifable part within reach of the catalytic centre of the lantibiotic modification enzymes (Annechien Plat, Leon D. Kluskens, Anneke Kuipers, Rick Rink, Gert N. Moll (2011) The N-terminal domain and a spacer are sufficient for functionality of the nisin leader peptide. Appl. Environ. Microbiol. 77, 604-611).

On the other hand, it has been reported for the lantibiotics mutacin (Chen P et al. FEMS Microbiol Lett. 2001; 195(2): 139), Pep5 (Neis S et al. FEMS Microbiol Lett. 1997; 149(2):249) and nisin (Van der Meer et al (1994) J. Biol. Chem. 269, 3555-3562.) that some of the conserved leader peptide residues are essential for the lantibiotic biosynthesis, whereas other residues are important for optimal biosynthesis rates.

In a preferred embodiment, a nucleic acid sequence encodes the leader peptide of a lantibiotic, for example the leader peptide of a lantibiotic selected from the group consisting of BacteriocinJ46, Lacticin481, SalivaricinB, Macedonin, StreptococcinAM49, StreptococcinAFF22, SalivaricinG32, Salivaricin9, MutacinII, Variacin, MukA1, MukA2/A3, MukA', Lacticin3147A1, StaphylococcinC55a, ButyrivibriocinOR79, RuminococcinA, BovicinHJ50, Thermophilin1277, CytolysinLL, CytolysinLS, Sublancin168, LichenicidinBeta, NukacinISK-1, NukacinKQU-131, SalivaricinA4, SalivaricinA5, SalivaricinA2, SalivaricinA, SalivaricinA3, SalivaricinA1, PlantaricinWb, HaloduracinA2, Lacticin3147A2, StaphylococcinC55b, Gallidermin, StaphylococcinT, Epidermin, NisinZ, NisinQ, NisinF, NisinA, EricinA, EricinS, Subtilin, NisinU, Epicidin280, Pep5, EpilancinK7, SWLP1, Streptin, LichenicidinAlpha Mersacidin, Actagardine, BHT-A2, SmbB, BHT-A1, SmbA, PlantaricinASM1, PlantaricinWa, HaloduracinA1, Mutacin1140/III, MutacinI, MichiganinA, Cinnamycin, LactocinS, AmfS (S. griseus), SapB, AmfS (S. avermitilis) RamS2, RamS1, LabyrinthopeptinA1/A3, LabyrinthopeptinA2 or a homolog of any of these leader peptides that allows for recognition and modification of the downstream located peptide of interest by the desired lantibiotic-modifying enzyme(s). The homolog shows at least 70%, preferably at least 80%, more preferably at least 90%, like 92%, 95% or even 98% sequence identity to the sequence one of the leader peptide sequences shown in Tables 1 and 2 of WO2006/062398, to one of the leader peptide sequences mentioned in Plat et al., (2010). Appl. Environ. Microbiol. 77, 604-611, or to leader peptides mentioned in Li, et al. (2010). Proc Natl Acad Sci USA. 107:10430-5.)

For example, the leader peptide can be a truncated or mutated lantibiotic leader peptide that is still capable of inducing post-translational modification of the peptide of interest. The leader does not need to have the capacity to induce translocation by a lantibiotic transporter like LanT, since this function can be taken over by a non-lantibiotic export signal that can be present in the polypeptide of the invention. In a specific aspect the leader peptide is the nisin leader peptide or a truncated or mutated version thereof wherein up to 4 amino acids at the N-terminus and/or wherein any one up to 5 amino acids at the C-terminus is mutated.

The lantibiotic leader sequence is followed by a peptide to be modified. The modification involves dehydration, preferably followed by cyclization. Cyclization may be performed by the host cell itself, provided that the relevant enzyme machinery is present. Alternatively, dehydrated peptides can participate in cyclization by reaction of dehydro amino acids to cysteine at high pH.

It will be clear that the peptide of interest can be any peptide whose modification by a dehydrating and ring forming lantibiotic enzyme is desired. Typically, a peptide of interest is designed such that following post-translational dehydration of one or more serine or threonine residues, the dehydrated residues can be coupled to a cysteine (either by a host cell or in vitro) such that a thioether ring structure is formed. Herewith, it is possible to introduce a stabilizing ring structure at essentially any desired position in the peptide. Of particular interest are peptides with a biological activity, e.g. peptides are intended for therapeutic use, because the introduction of one or more thioether rings generally increases the biostability of the peptide. Furthermore, a ring structure may be used to alter the biological activity, for instance receptor binding affinity or enzyme specificity, of a peptide. The peptide of interest is for example a hormone, an enzyme inhibitor, an enzyme activator, a receptor ligand, an inhibitory peptide, a lantibiotic protein, a viral protein, a eukaryotic protein, a mutant thereof (e.g. specifically designed to allow for a modification at a certain position), a mimic, a homologue or a functional fragment equivalent thereof.

Examples of such peptides are glucagon-(1-29), incretin/ gastrin inhibitory peptide, enterostatin, nesfatin-1, angiotensin-(1-9), apelin 12, ACTH-(1-24), leptin 22-56, IL-1α (223-250), IL-16 (208-240), Glucagon like peptide 1, glucagon like peptide-2 (1-33), neuropeptide S, delta sleep inducing peptide, galanin like peptide, melanin concentrating hormone, cerebellin, neuropeptide W-23, neuropeptide W-30, kinetensin, galanin, CART-(62-76), cortistatin 17, melanotropin potentiating factor, salusin-β, neuropeptide Y, atrial natriuretic factor, brain natriuretic peptide, dendroaspis natriuretic peptide, c-type natriuretic peptide-(32-53), C-type natriuretic peptide-(1-53), vasonatrin, calcitonin, C-procalcitonin, N-procalcitonin, osteocalcin, pTH (1-38), pTH-related protein-(1-40), preptin, osteostatin (1-5), growth hormone releasing factor, W3R5 ghrelin 1-5, human growth hormone-(1-43), KGF receptor peptide, epidermal mitosis inhibitory pentapeptide, BPP tuna muscle, hirudin-(54-65), bradikinin, urotensin II, angiotensin A, renin inhibitor, angiogenin-(118-123), platelet factor 4-(58-70), endothelin 1-(11-21), big endothelin-(19-37), thymosin 64 (16-38), salusin-beta, alloferon 1, cortistatin 29, tuftsin, c-reactive protein-(174-185), CKS 17, pseudin 2, anti inflammatory peptide 1, characteristic MSH-Tetrapeptide, procollagen Type I, thrombin receptor binding peptides, thrombospondin-1 fragments, laminin fragments, IFN-α receptor recognition peptide 1, azurin fragments, valorphin, nociceptin, alpha casein 90-96, beta casomorphin, α-neoendorphin, gluten exorphin A5, gluten exorphin B5, gluten exorphin C, dynorphin A, alpha endorphin, beta endorphin, hemopressin, Galanin-(1-19), somatostatin, adrenomedullin, annexin A1, bombesin, bradikinin potentiator B, bradikinin potentiator C, caerulein desulfated, calcitonin gene related peptide, cholecystokinin, exendin 3, exendin 4, acetalin, substance P, corticotropin release factor, deltorphin II, dermorphin, eglin c, eledoisin, endomorphin 1, endomorphin II, GMAP 16-41, GIP 6-30, helodermin, hemokinin I, hylambatin, intermedin, kassinin, allatostatin, calpastatin-(184-210), kinogen based thrombin inhibitor, kisspeptin, LL37, mastoparan, neuropeptide E1, melittin, morphin modulating peptide, α-melanotropin (MSH), neuroendocrine egulatory Peptide-1/2, neurokinin A/B/C, neurostatin, neuropeptide FF, neuropeptide Y, neurotensin, obestatin, oxytocin, orphan GPCR SP9155 agonist p518, pancreastatin, pancreatic polypeptide, peptide T, peptide YY, physalaemin, PACAP-27, pneumadin, prolactin-releasing peptide, salusin-α, sauvagine, scyliorhinin I/II, secretin, substance P, thymosin α1, thymosin β4, thymosin β10, trail mimetics, urocortin I/II/III, urotensin I/II, vasopressin, PHM-27, VIP, amylin, anti fibrin polymerant, GHRH, IGF-1, IGF-2, RELAXIN-1/2/3, insuline like peptide-3/4/5/6, histatin-5, indolicidin, magainin I, C-type natriuretic peptide, vasonatrin, delta sleep inducing peptide, alpha-dendrotoxin, echistatin, defensin I, urocortin, small cardioactive peptide A and B, ceratotoxin A, cerebellin, charybdotoxin, conopressin G, alpha-conotoxin E1, corazonin, leu-enkephalin, met-enkephalin, gonadoliberin II, tocinoic acid, corticotropin inhibiting peptide, corticotropin release factor, peptide XY, brain derived acidic fibroblast growth factor, brain derived basic fibroblast growth factor, human growth hormone, growth hormone release factor, guanylin, intercellular adhesion molecule, HIV antigenic peptide gp120, HIV antigenic peptide I fragment (gp 41), HIV antigenic peptide 5, HIV protease inhibitors, insulin-like growth factor-I, IGF II 69-84, interleukin fragment, interleukin II fragment, leukokinin I, leukopyrokinin, motilin, neuropeptide Y, endorphin, ras oncogene related peptide, erythropoetin fragments, epidermal growth factor, transforming growth factor, leucinostatins, nerve growth factor, gluten exorphins, pardaxin, tyrocidin, mast cell degranulating peptide, tumor necrosis factor, RGD peptides, thymopoietin, tachikinin, cecropin, any viral polypeptide or a peptide obtained by using semi randomized primers in which serine/threonine and—if desired—cysteine residues are present.

The peptide can be also be a (mutant of an above mentioned) lantibiotic, a (mutant of a) non-lantibiotic bacteriocin, for instance of bavaricin MN, enterocin P, mesentericin Y105, pediocin PA-1, lactacin F, lactococcin G, plantaricin EF, plantaricin JK, lactococcin A, lactococcin 972, plantaricin A, curvacin A, divercin V41, enterocin A, muntcidin, sakacin P, leukocin A, carnobacteriocin B2, clostticin 574, circularin A, microcin J25, gassericin A or AS48. The lantibiotic or bacteriocin may or may not comprise its own leader peptide. Of course, if it comprises its own leader peptide in addition to the lantibiotic leader peptide as defined above, the distance between the leader peptide to be recognized by the dehydratase and the residues to be modified becomes relatively large. For that reason, it may be preferred to remove its own leader peptide such that in the whole polypeptide construct only one lantibiotic leader is present. In certain situations, for instance if the own leader peptide is small, as is for example the case for circularin A, microcin J25, gassericin A and AS48, the presence of an additional leader sequence may not negatively affect modification of the peptide of interest. It can even be envisaged that the presence of distinct leader peptides (e.g. lantibiotic leader peptide as well as bacteriocin leader peptide) is advantageous because this allows for the recognition and modification by distinct modifying enzymes.

A nucleic acid construct provided herein is further characterized by the presence of, 3' from the encoded peptide sequence to be modified, a sequence encoding a said cell wall-spanning domain. This domain can span for instance the peptidoglycan layer of a Gram-positive host cell and thus ensures that the modified amino acid sequence is displayed on the cell surface of the host cell. Very suitable spacer domains can be derived from or based on the cell wall-spacing domain of a multi-domain, cell-envelope proteinase of a lactic acid bacterium. Typically, said spacing domain contains several repeats of similar or even identical amino acid stretches. In one embodiment, said cell-wall spacing domain comprises the amino acid sequence of a cell wall-spacing domain of Protein A (PrtA) of *Staphylococcus aureus*, prtH of *Lactobacillus helveticus*, prtP of *Lactococcus lactis*, scpA of *Streptococcus pyogenes* or csp of *Streptococcus agalactiae*, or a functional analog or fragment thereof capable of spanning the cell wall of the host cell on which it is to be displayed (Siezen, 1999. Multi-domain, cell-envelope proteinases of lactic acid bacteria. A. van Leeuwenhoek 76:139-155). In a specific aspect, the nucleic acid construct includes only the coding regions of either *Staphylococcus* protein A or a Streptococcal protein G that are responsible for cell wall spanning and membrane anchoring (see e.g. Navarre and Schneewind, 1999. Surface proteins of Gram-positive bacteria and mechanism of their targeting to the cell wall envelope. Microbiol. Molecul. Biol. Rev. 63:174-229).

The cell wall-spanning domain is followed by a sortase motif. Sortase, an enzyme involved in the covalent linkage of some surface proteins of *Staphylococcus aureus* to the peptidoglycan, plays a key role in the display of surface proteins and in the virulence of this important human pathogen (Marraffini et al., 2006: Microbiol. Mol. Biol. Rev. 70:192-221). The covalent linkage is dictated by a sorting signal referred to as "sortase recognition motif" or "sortase motif", followed by a hydrophobic domain made of about 20 amino acids and a tail of positively charged amino acids. Sortase motifs are known in the art, see (1999) Microbiol Mol Biol Rev 63:174-229, pmid:10066836 or U.S. Pat. No. 7,238,489. This mechanism has been reported in many Gram-positive bacteria. The optimal motif may depend on the host cell to be used. FIG. 1C shows the consensus sequence of a sortase motif for *L. lactis* (panel A) and *S. aureus* N315 (Panel B). In one embodiment, the sortase-recognition motif comprises the amino acid sequence LPXTG wherein X may be the amino acid D, E, A, N, Q, or K, preferably wherein said sortase-recognition motif consists of LPKTG.

The sortase motif is followed, optionally via a spacer sequence, by a hydrophobic domain capable of spanning the lipid bilayer of the host cell. The membrane spanning domain typically has a length of 20 to 30 amino acids. Preferred residues include Ala, Pro, Gly, Phe, Leu, Ile, Val, Met. In one embodiment, the membrane spanning domain comprises the sequence PAFG, FGFL, LGVIV, VIVVIL, ILMGV and/or GVLGL. In a specific aspect, it comprises the sequence PAFGFLGVIVVILMGVLGL.

The modification and export of the leader construct is in several aspects highly surprising:

1) The modification of this C-terminally immobilized polypeptide is surprising. There are no previous reports on the modification of N- or C-terminally immobilized peptides by lantibiotic enzymes. The polypeptide is anchored to the membrane via the hydrophobic segment close to its C-terminus. This means that the C-terminus is not free and that the peptide is fixed. In native nisin 8 positions are dehydrated and 5 rings are installed. Hence, either the peptide has to move along the enzyme or the enzyme along the peptide. This modification is surprising since movement of the peptide and modification enzymes along each other might be hindered by the C-terminal immobilization due to the membrane anchoring. Indeed hindrance is taking place since a mass peak with 8 dehydrations is completely absent, which is in contrast to native nisin which is 8-fold dehydrated with only Ser33 escaping in 10% of the cases dehydration (Post-translational modification of nisin. The involvement of NisB in the dehydration process. Karakas Sen A, et al. Eur J. Biochem. 1999 261:524-32.) Despite this hindrance surprisingly 7, 6 and 5 fold dehydration (FIG. 7C) still occurs.

2) The export is surprising because of the length of the polypeptide. In the scientific literature the largest peptide modified by lantibiotic enzymes is 48 amino acids (Production of dehydroamino acid-containing peptides by *Lactococcus lactis*. Rink R, et al. Environ Microbiol. 2007 73:1792-6). The present modified and exported construct is 186-210 amino acids long, which is nearly 4-fold longer than the longest lantibiotic-enzyme-modified peptide reported up to now.

3) The export is not blocked by the hydrophobic segment close to the C-terminus. The nisin leaderpeptide is hydrophilic and if a leaderpeptidase is present the leaderpeptide is found back in the medium i.e. it does not stay attached to the membrane or to the cell wall. This indicates that the nisin transporter forms an aqueous channel. This is in contrast to other signal peptides e.g. the sec and tat signal peptides which have segments that are that hydrophobic that they stay in the membrane. In the latter case signal peptidases are required to release the transported peptide or protein into the medium. With the used construct which has a hydrophobic sequence close to the C-terminus, one would expect that this hydrophobic sequence which anchors the polypeptide in the membrane blocks the transport via the lantibiotic transporter. Unexpectedly, the export of the polypeptide is not blocked at all by the hydrophobic membrane anchor but taking place via a lantibiotic transport system. Since the sortase which recognizes the LPXTG motif is located at the outside of the cell membrane it is equally surprising that the polypeptide apparently is substrate for the sortase action which couples the polypeptide to the cell wall.

4) The export of intact polypeptide is surprisingly enhanced by the combination of the lantibiotic transporter, the hydrophobic segment close to the C-terminus and the charged very C-terminal amino acids KRKQREE. As clearly demonstrated in example 4, C-terminal truncations lead to degradation. This likely results from inefficient export allowing intracellular peptidases to degrade the polypeptide precluding its intact transport.

The very C-terminus of the encoded proteinaceous substance consists of a charged tail for membrane anchoring. In one embodiment, said charged membrane anchoring domain has a length of at least four amino acid residues, preferably wherein at least 50% of the residues are positively charged amino acids, more preferably Lys and/or Arg residues.

It may be advantageous that the fusion peptide comprises one or more additional sequence motifs. For example, at least one proteolytic cleavage site can be introduced between elements (b) and (c) such that the modified peptide can be released after post-translational modification and surface display. Useful cleavage sites are known in the art, and include a factor Xa protease recognition site, like the amino acid sequence IEGR.

A further aspect relates to an expression vector comprising a nucleic acid construct according to the invention. Preferably, the vector is designed for expression of the construct in a Gram-positive host cell. For example, it comprises one or more of the following elements: the sequences for the inducible NisA promoter, nisin leader peptide, nisin, and the LPXTG cell wall-anchoring motif of the L. lactis PrtP protease.

Also encompassed is a Gram-positive host cell comprising such an expression vector and being capable of post-translationally modifying said a polypeptide of interest to a dehydroresidue- or thioether bridge-containing polypeptide. The host cell is for instance a lactic acid bacterium, preferably selected from Lactococcus lactis, Bacillus subtilis, Streptococcus pyogenes, Staphylococcus epidermis, Staphylococcus gallinarium, Staphylococcus aureus, Streptococcus mutans, Staphylococcus warneri, Streptococcus salivarius, Lactobacillus sakei, Lactobacillus plantarum, Carnobacterium piscicola, Enterococcus faecalis, Micrococcus varians, Streptomyces OH-4156, Streptomyces cinnamoneus, Streptomyces griseoluteus, Butyrivibrio fibriosolvens, Streptoverticillium hachijoense, Actinoplanes linguriae, Ruminococcus gnavus, Streptococcus macedonicus, Streptococcus bovis, containing the relevant lantibiotic biosynthesis enzymes and transporter e.g. NisB, C, T or SpaB, C, T. Of particular interest is a library of host cells comprising a plurality of host cells according to the invention, wherein each member of said library displays at its cell surface a different dehydroresidue- or thioether-bridge-containing polypeptide. The library is very advantageously used to screen for novel useful cyclic peptides, like novel cyclic affinity tags, cyclic biologically active peptides, such as peptide drugs, receptor ligands, cyclic inhibitory peptides. Advantageously, the construction of a library involves the use of degenerate codons incorporated during oligonucleotide synthesis that include mixtures of nucleotides at each position. For example, the complete set of standard amino acids is encoded using NNK or NNS codons, wherein N is A, T, C or G and K=G or T and S=C or G, thus excluding the TAA or TGA stop codons. Host cells expressing the candidate affinity tags can be contacted with an immobilized binding partner to select for high affinity binding sequences. Thus, also provided is a method for identifying a dehydroresidue- or thioether-containing polypeptide capable of binding to a target entity of interest, which method comprises the steps of: (a) providing a library as described above; (b) selecting from the library at least one host cell displaying a dehydroresidue- or thioether-containing polypeptide capable of binding to the target entity of interest; and (c) identifying the polypeptide sequence displayed on said at least one selected host cell.

In a specific aspect, the library comprises a plurality of candidate cyclic affinity tag sequences, for example variants of cyclic streptavidin tag (Strep tag). Provided is a method for identifying a cyclic streptavidin tag (Strep tag) comprising a thioether-bridge capable of binding to biotin, which method comprises the steps of:
(a) providing a library of host cells comprising a plurality of Gram-positive host cells comprising an expression vector according to the invention and capable of post-translationally modifying a polypeptide of interest to a thioether-bridge-containing polypeptide, wherein the polypeptide comprises the amino acid sequence Ser/Thr-(Xaa)$_n$-Cys or Cys-(Xaa)$_n$-Ser/Thr, wherein Xaa is any amino acid and n is 1-5, preferably n is 3; (b) selecting from the library at least one host cell displaying a thioether-bridged peptide with affinity to streptavidin (Strep-tag) using immobilized streptavidin; and (c) identifying the polypeptide sequence displayed on said at least one selected host cell. For example, after two rounds of magnetic selection (MACS) using streptavidin-coated magnetic beads, the selected bacteria can be plated for analysis.

The host cell may also be used as a reporter system for assessing lantibiotic biosynthetic enzyme and/or transporter activity, wherein efficient cell surface expression of a thioether-bridge containing peptide is merely used as a read-out. Cell surface expression can be detected by methods known in the art, including antibody detection and immobilization to a solid support.

LEGENDS TO THE FIGURES

FIG. 1A: Genetic organization of the display vectors used in this study. P$_{nisA}$, nisin inducible promoter; leader, nisin leader peptide; NisA, coding sequence pronisin; FXa, Factor Xa recognition site; Strep-tag, streptavidin recognition sequence; 3C, human rhinovirus protease recognition sequence. Cell wall spacer and cell wall anchor of L. lactis PrtP protease (amino acids 1789-1912). (a) an N-terminal a lantibiotic leader sequence; (b) an amino acid sequence of interest to be post-translationally modified to a dehydroresidue- or thioether-bridge containing polypeptide; (c) a hydrophilic cell-wall spanning domain; (d) a sortase recognition motif; (e) a hydrophobic membrane spanning domain; and (f) a C-terminal charged membrane anchoring domain. The corresponding (poly)peptide products are termed with identical name without preceding "p".

Figure 1B:
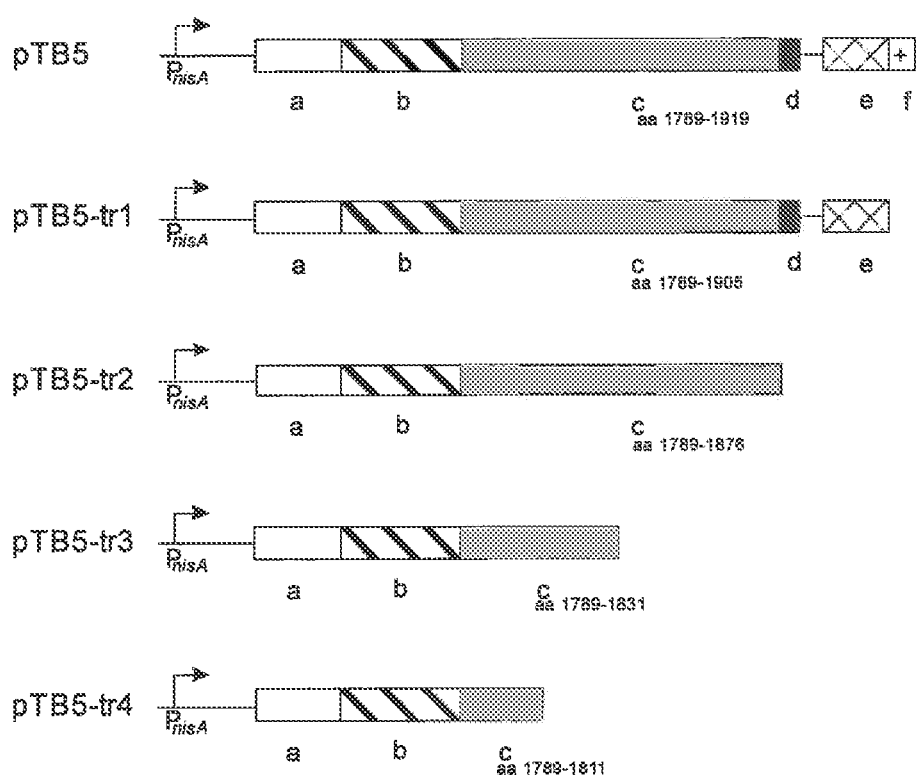
Figure 1C:
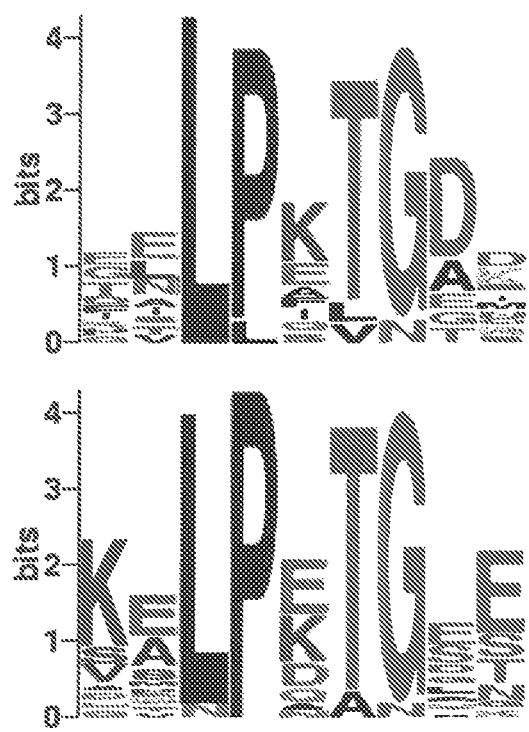

FIG. 1B: Genetic organization of truncated pTB5 variants. aa## indicates amino acid numbering of the cell wall anchor of the L. lactis PrtP protease. (a) an N-terminal a lantibiotic leader sequence; (b) an amino acid sequence of interest to be post-translationally modified to a dehydroresidue- or thioether-bridge containing polypeptide; (c) a hydrophilic cell-wall spanning domain; (d) a sortase recognition motif; (e) a hydrophobic membrane spanning domain; and (f) a C-terminal charged membrane anchoring domain FIG. 1C: Consensus sequences of LPXTG motifs. Upper panel: consensus for Lactococcus lactis; lower panel: consensus for Staphylococcus aureus N315.

Figure 2:
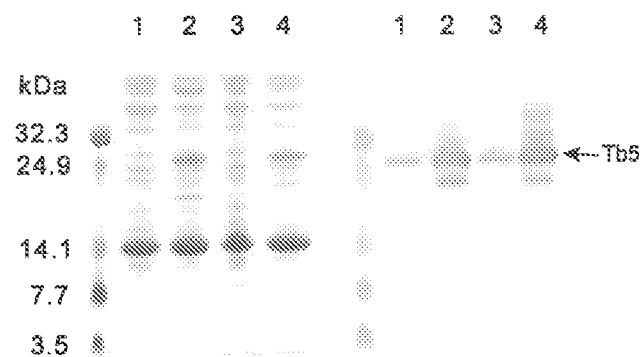

FIG. 2. Expression of the fusion peptide construct. A) Coomassie stained 12% SDS-PAA gel, and B) Western analysis with anti-nisin leader antibodies of L. lactis NZ9000 cell extracts with plasmids: 1, pTB5, uninduced; 2, pTB5 induced; 3, pTB5/pIL3BTC, uninduced; 4, pTB5/pIL3BTC, induced.

Figure 3:
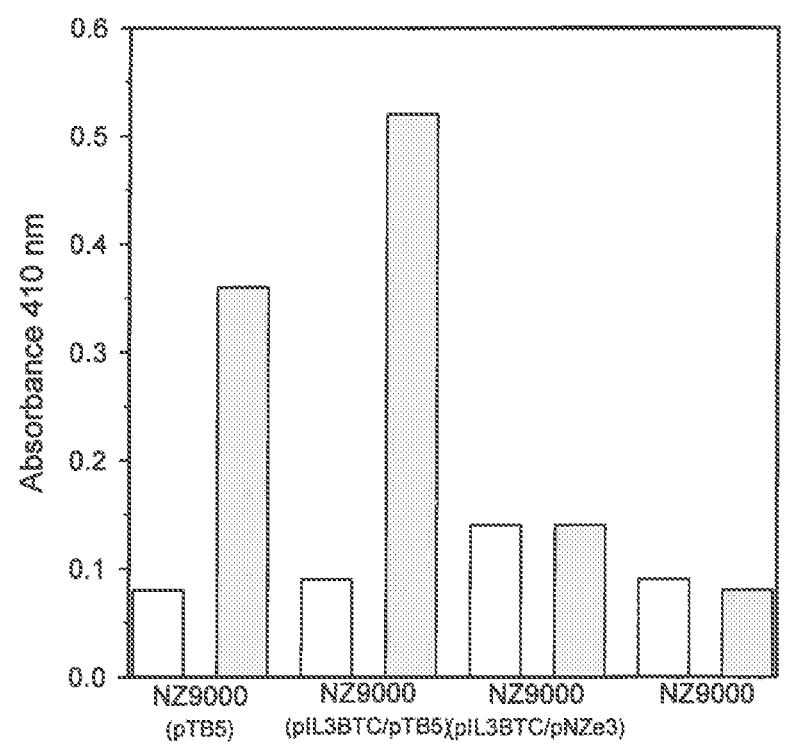

FIG. 3: Cell surface location of fusion peptide construct. Whole cell ELISA on L. lactis NZ9000 cells for detection surface displayed prenisin anchor fusion protein. Rabbit anti-nisin leader antibodies were allowed to bind to lactococcal cells displaying TB5. Alkaline phosphatase conjugated goat anti-rabbit IgG was added and a color was generated by the addition of p-nitrophenylphosphate. White bars, uninduced cells; grey bars, induced cells.

Figure 4:
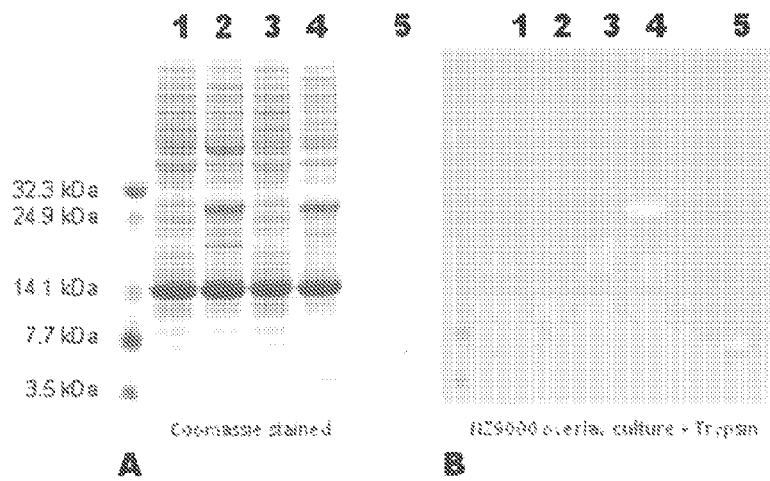

FIG. 4. Display of modified prenisin on the cell surface. Panels AB: Two parallel SDS-PAA gel analyses of cell extracts from L. lactis NZ9000 with or without modifying enzymes. 1, pTB5, uninduced; 2, pTB5 induced; 3, pTB5/pIL3BTC, uninduced; 4, pTB5/pIL3BTC, induced; 5, prenisin. Panel A) Coomassie-stained 12% SDS-PAA gel. Panel B) 12% SDS-PAA gel with an overlay of a nisin-sensitive L. lactis NZ9000 strain with 0.1 mg/ml trypsin. The halo in lane 4 of gel B at the site of the induction-dependent Coomassie-stained protein band proves that the prenisin part of the fusion protein is modified by NisB and NisC. Panel C): Analysis of lactococcal cells displaying active nisin with an overlay culture of a nisin-sensitive *L. lactis* strain with trypsin (left panel), or with a NisP-producing *L. lactis* strain (right panel). NisP specifically cleaves off the nisin-leader yielding active nisin. Growth inhibition, seen as a halo (white circles/rims in FIG. C), of this strain clearly demonstrates that NisB and NisC correctly modified prenisin and formed at least ring A, B, and C of TB5 (TB5 is in the FIG. 4C indicated as N15).

FIG. 5. Cell surface display of NisBC-modified cAng-(1-7).
A: Whole cell ELISA on *L. lactis* NZ9000 cells for detection surface displayed leader-angiotensin(1-7) fusion protein. Rabbit anti-nisin leader antibodies were allowed to bind to lactococcal cells displaying TB2. Alkaline phosphatase conjugated goat anti-rabbit IgG was added and a color was generated by the addition of p-nitrophenylphosphate. White bars, uninduced cells; gray bars, induced cells.
B: Coomassie stained 12% SDS-PAA gel, and Western analysis with anti cyclic-angiotensin-(1-7) antibodies on total protein extracts of *L. lactis* NZ9000 with plasmid: lane 1, pTB2; lane 2, pTB2 and pIL3BTC.
C: MALDI-TOF spectrometry of thioether-bridged angiotensin-(1-7) anchor fusion peptide TB3 shows single dehydration. The relevant peptide fragment (STKDFNLDLVS-VSKKDSGASPRIEGRDRVSIHCGGGWSHPQFEKEAL-FQ) is schematically shown. Mass peak of 5398.83 corresponded to the singly dehydrated N-terminal TB3 fragment.
D: MALDI-TOF spectrometry showing no CDAP addition to thioether-bridged angiotensin-(1-7) anchor fusion peptide TB3. The upper two figures show a clear mass shift of 25 Da for the control peptide which is indicative for addition of CDAP to this peptide. No mass shift was found for TB3 (lower two figures) indicating the absence of a free cysteine residue and thus proving the presence of a thioether bridge in TB3.

Figure 6:
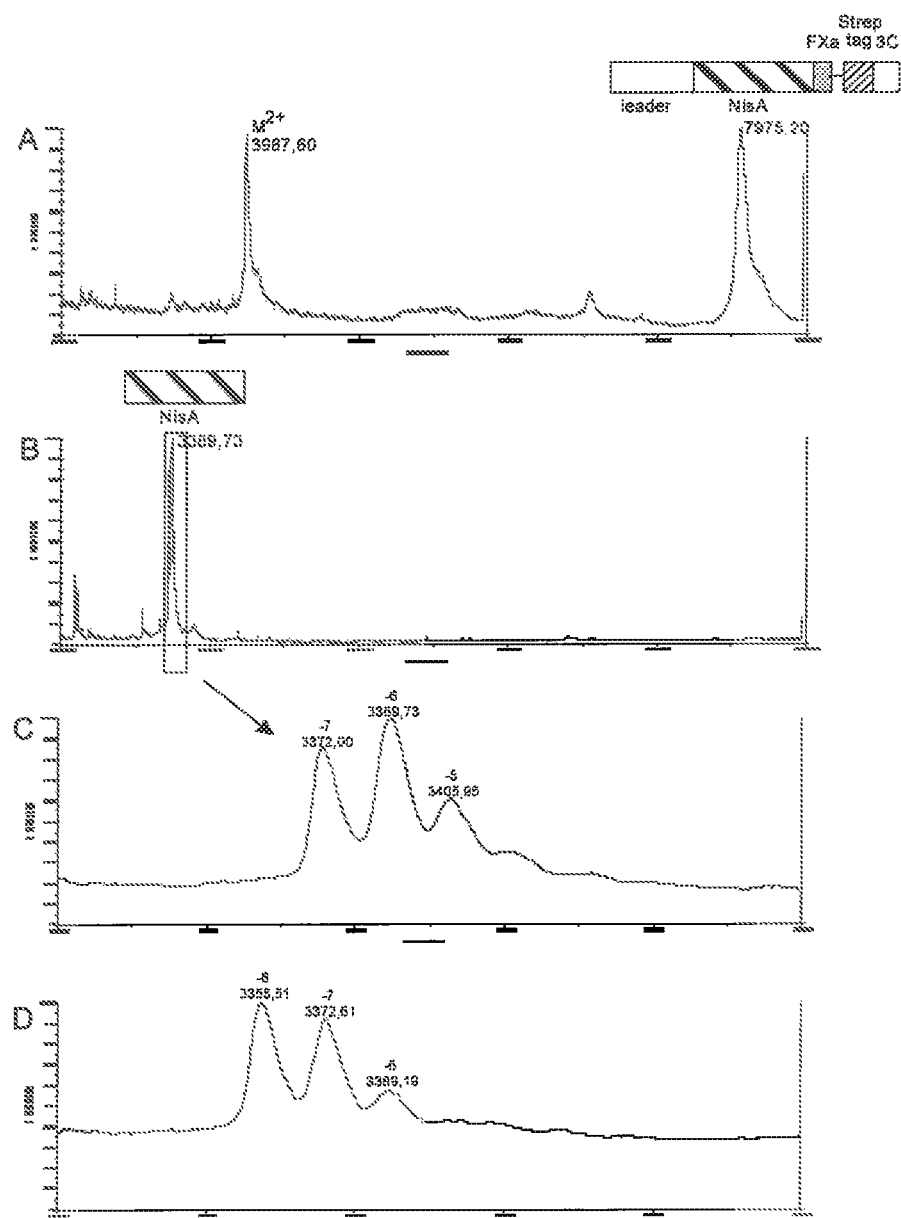

FIG. 6: MALDI-TOF spectrometry of nisin-anchor fusion peptide TB1. A) purified TB1. B) purified TB1 treated with trypsin. C) Boxed area of B in more detail. Nisin part of TB1. Number of dehydrations are indicated with −7, −6 etc. D) Supernatant of *L. lactis* NZ9000(pIL3BTC/pNZe3) treated with trypsin. Number of dehydrations are indicated with −8, −7 etc. In FIGS. A and B the relevant peptide fragment is schematically shown.

Figure 7:
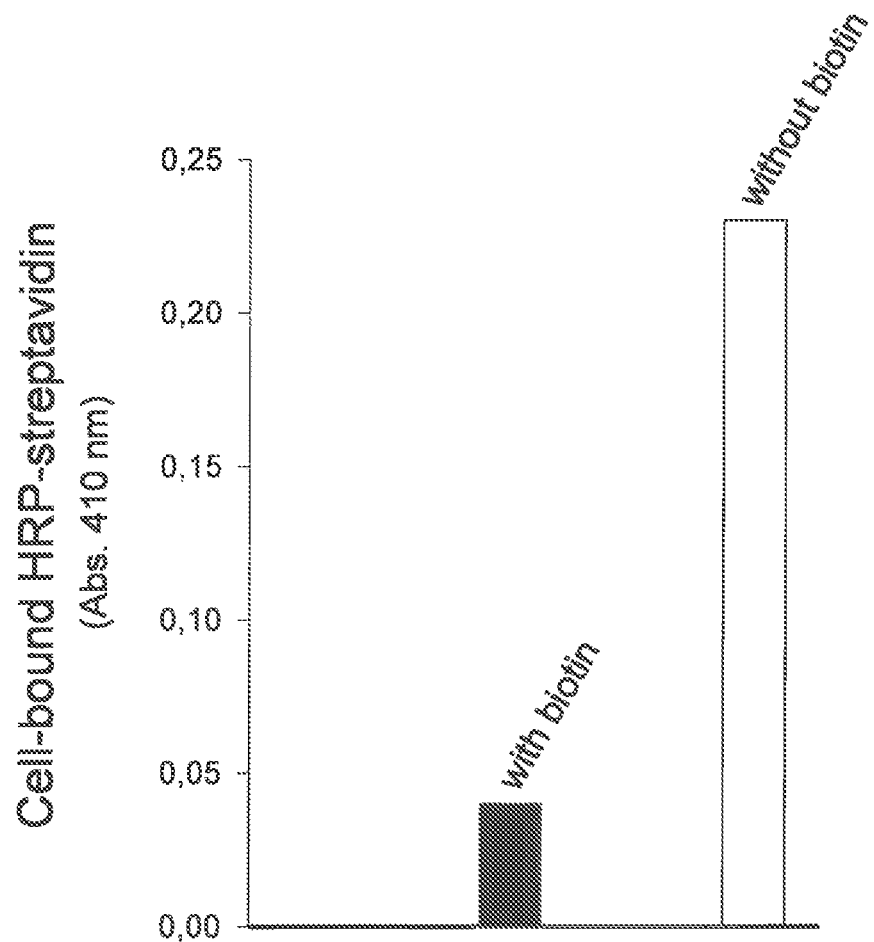

FIG. 7: Display of selected streptavidin binding peptide RND-X3-1.
pRND-X3-1 is presented in FIG. 1A. Whole cell ELISA on *L. lactis* NZ9000(pIL3BTC) displaying RND-X3-1 with or without co-incubation with Biotin. Displayed peptide was detected with HRP conjugated streptavidin with ABTS/$H_2O_2$ as substrate solution. Experiment was repeated in more than three independent experiments with differences ≤15%.

Figure 8:
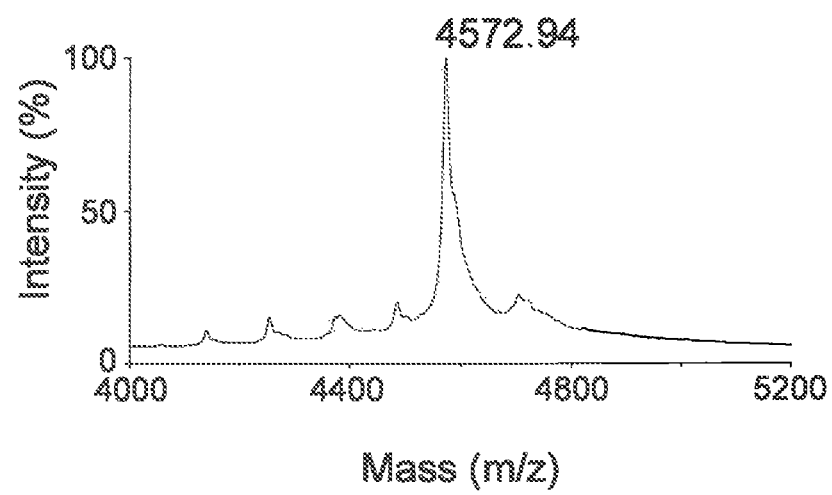
Figure 8:
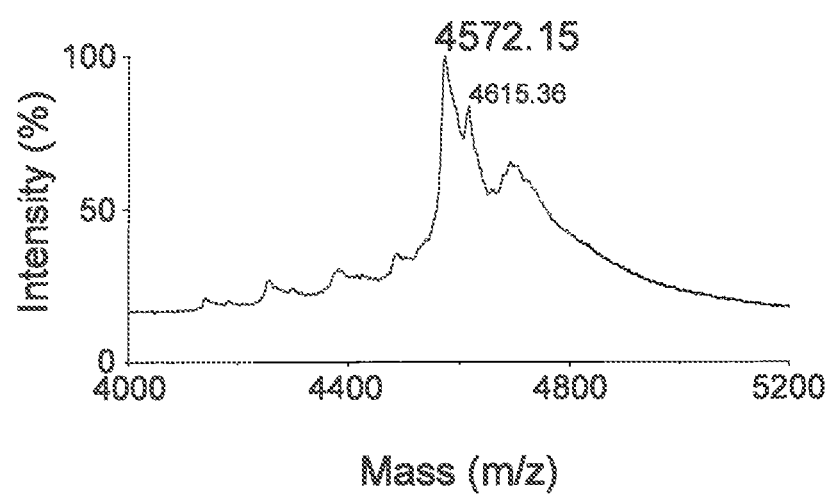

FIG. 8: MALDI-TOF spectrometric analysis of 1-Cyano-4-dimethylaminopyridinium tetrafluoroborate (CDAP) addition to the streptavidin-selected thioether-bridged peptide (see Example 7). For analysis a translation termination codon was inserted in between the peptide and anchor sequence in pRND-X3-1 (FIG. 1A) and the resulting plasmid was termed pTB9 (FIG. 1A). The N-terminal part in front of the termination codon thus encodes the nisin leaderpeptide, MSTKDFNLDLVSVSKKDSGASPR, fused to a modifiable peptide ISNMVCNMKTATCHCSIHVSK. Growth medium from cells containing plasmid pTB9 encoding this construct with the termination codon and containing pIL3BTC was spotted onto the MALDI target plate and analysed by Maldi TOF. A control experiment with a control peptide containing a free cysteine shows a clear mass shift of 25 Da for the control peptide which is indicative for addition of CDAP to the control peptide. The present experiment shows production of peptide with a mass of 4572.94 Da which corresponds to the four-fold dehydrated peptide (theoretical average mass without N-terminal methionine: 4570.346 Da). Most likely, the penultimate serine in this nisin-related peptide escaped dehydration analogously to the case of Ser29 in nisin itself. In the presence of CDAP, no 25 Da mass shift was found for the selected TB9-peptide which indicates the absence of a free cysteine residue and thus proving the presence of a thioether bridge.

EXPERIMENTAL SECTION

Example 1

Expression Vector for Cell Surface Display of Thioether and Dehydroresidue-Containing Peptides on *Lactococcus Lactis*

Objective:
This example concerns the construction of an expression vector for surface display of thioether-containing peptides on *Lactococcus lactis*. The *L. lactis* host organism provides the nisin biosynthesis and export machinery for introduction of the thioether linkages in the desired peptide and its export. The peptide is translationally fused to a LPXTG cell wall-anchoring motif such as that of the *L. lactis* PrtP protease. This anchoring mechanism requires processing by a sortase for covalent anchoring of the peptide to the peptidoglycan of the bacterial cell wall. In this way the peptide and the encoding DNA are linked allowing selection/screening for post-translationally modified peptides with desired properties. Nisin will be used as a model peptide for development and demonstration of the display system.

Materials and Methods
The LPXTG cell wall-anchoring motif of the *L. lactis* PrtP protease was translationally fused by PCR to the nisA gene in pNZE3, a derivative of the lactococcal expression vector pNG8048. The relevant parts of the display vector comprise the sequences for the inducible NisA promoter, nisin leader peptide, nisin, and the LPXTG cell wall-anchoring motif of the *L. lactis* PrtP protease (FIG. 2A). The display vector was electroporated to *L. lactis* NZ9000(pIL3BTC). The latter provides the nisin biosynthesis enzymes NisB, NisC, and the transporter NisT. Production of the nisin-anchor protein was analyzed by SDS-PAGE, and Western blotting using anti-nisin leader antibodies.

Results.
A lactococcal display vector was constructed with the correct nisin-anchor sequence under control of the NisA promoter. This display vector was designated pTB5. *L. lactis* NZ9000 (pIL3BTC/pTB5) cells were grown in the absence or presence of nisin to allow production of TB5. An equal number of cells was digested with lysozyme and solubilized in SDS-PAGE sample buffer. Proteins in the cell extracts were separated by SDS-PAGE and visualized by Coomassie staining (FIG. 2, left panel). Comparing cell extracts from uninduced and induced cultures showed the presence of a protein band of about 26-28 kDa in the induced culture. Western blot analysis with anti-nisin leader antibodies demonstrated that this protein is nisin-anchor fusion protein TB5 as seen by the strong immunoreactive signal (FIG. 2 rightside panel). The observed molecular weight of TB5 differed from the theoretical calculated molecular weight of 18 kDa. This difference in migration is most likely due to the covalent attachment of peptidoglycan fragments to TB5. The measureable but less strong immunoreactive signal in the uninduced cultures is due to a little leakage of the nisin promoter. All together, lactococcal cells containing the constructed display vector, pTB5, directed the production of TB5 when induced with nisin.

Example 2

Anti-Leaderpeptide Antibodies Demonstrate the Cell Surface Location of the Cell Wall Attached Prenisin Anchor Fusion Protein TB5

Objective:
Display of TB5 at the cell surface of *L. lactis* was evaluated with a whole cell ELISA using anti-nisin leader antibodies.
Materials and Methods
*L. lactis* NZ9000(pTB5) and *L. lactis* NZ9000(pIL3BTC/pTB5) cells were grown with and without nisin for induction of TB5. After production cells were collected by centrifugation, washed three times with phosphate buffered saline, pH 7.4 (PBS). An equal number of cells displaying TB5 are incubated with a 1000-fold diluted rabbit anti-nisin leader antibody solution in a final volume of 1 ml PBS plus 0.5% BSA at room temperature for 1 hour under rotation. After washing three times with PBS displayed TB5 was visualized by incubation with alkaline phosphatase conjugated goat anti-rabbit IgG (1:10000) and p-nitrophenyl phosphate (0.5 mg/ml) as substrate. The absorbance was determined at 410 nm, which is a measure for the number of displayed TB5.
Results
The results summarized in FIG. 3 showed a positive color response for the induced *L. lactis* NZ9000(pIL3BTC/pTB5) cells. A lower level of color response was seen for the uninduced lactis culture. This proved that the nisin leader is accessible on the cell surface of *L. lactis*.

Example 3

Figure 4C:
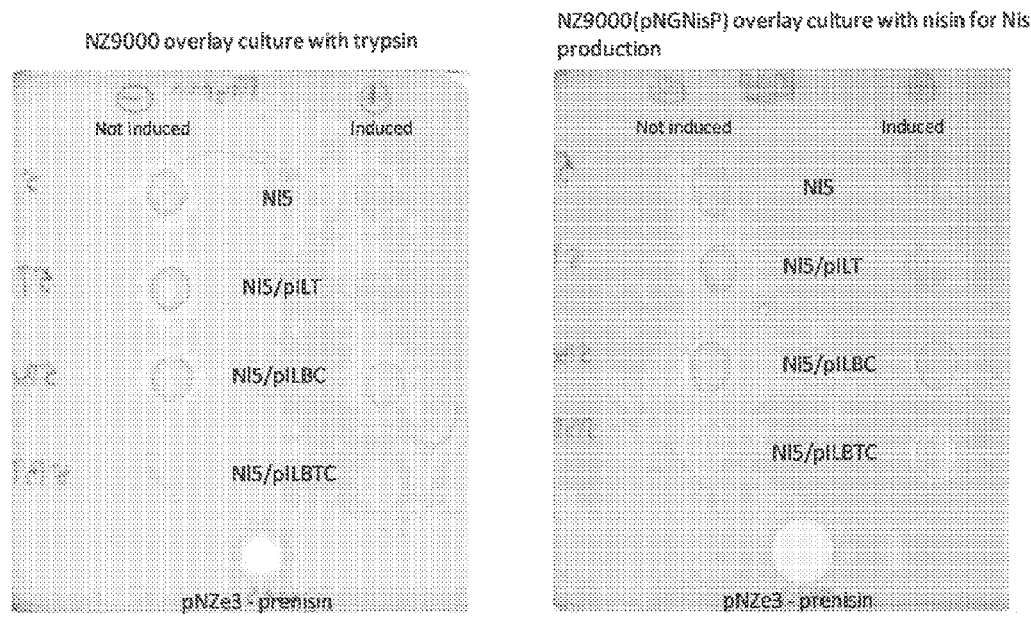

Prior to cell surface display the prenisin-anchor fusion protein has been modified intracellularly by NisB and NisC. Modification by NisB- and NisC-modified prenisin-anchor fusion protein was demonstrated by antimicrobial activity against overlaid cells after leader peptide cleavage.
Objective:
Example 2 shows that TB5 is produced resulting in the display of prenisin on the lactococcal cell surface. In this example the modification of nisin by NisB and NisC was evaluated with an overlay of a nisin-sensitive *L. lactis* strain. Growth inhibition of this strain indicated that NisB and NisC correctly modified and formed at least ring A, B, and C of TB5.
Materials and Methods
A GM17 agar plate with an extensively washed SDS-PAA gel or spots of pTB5 producing *L. lactis* NZ9000 cells was covered with a 200-fold diluted *L. lactis* MG1363 or NZ9000 strain in 0.5% top agar with 0.1 mg/ml trypsin. Trypsin is required for cleaving of the nisin leader yielding active nisin. The agar plates were incubated overnight at 30° C.
Results
FIG. 4 showed two similar SDS-PAA gel analyses of cell extracts from *L. lactis* NZ9000 with or without modifying enzymes. The Coomassie stained gel (FIG. 4A) showed that TB5 was produced in induced cultures independent of the presence of the modification enzymes. Only TB5/BTC inhibited growth of the indicator strain, seen as a clearing zone (halo) in the overlay (FIG. 4B). This indicated that NisB and NisC correctly modified TB5 yielding active nisin. Similar results were obtained with overlay analysis on whole cells (FIG. 4C). Active nisin was found for TB5 producing lactococcal cells which contained modification en transport enzymes. Since the nisin leader is only accessible to trypsin from the outside, active nisin is displayed on the lactococcal cell surface. Furthermore, specific cleavage of the nisin leader by NisP, resulted in growth inhibition, suggesting that immobilized nisin is still antimicrobially active.

Summarizing, NisB and NisC correctly modified nisin-anchor fusion protein TB5 since active nisin was observed with a nisin-sensitive strain in an overlay on SDS-PAA gel and on whole cells. Hence, the anchor moiety of TB5 provided the signals for covalent attachment of TB5 to the peptidoglycan layer thereby displaying active nisin on the lactococcal cell surface.

Example 4

The complete membrane anchor is needed for stable display of NisB and NisC modified peptide.
Aim:
release of truncated prenisin anchor constructs to facilitate mass spectrometric analyses.
Methods
Complete protein 186 amino acids: MSTKDFNLDLVS-VSKKDSGASPRITSISLC TPGCKTGALMGCNMK-TATCHCSIHVSKIEGRGQSLKTKVAAAVEAAKTVGK-GDG TTGTSDKGGGQGTPAPAPGDIGKDKG-DEGSQPSSGGNIPTNPATTTSTSTDDTTDR NGQLTS-GKGALPKTGETTERPAFGFLGVIVVILMGVL-GLKRKQREE Four truncated variants were prepared see FIG. 1B:

pTB5-tr1
Immediately upstream charged membrane tail (KRKQREE)
MSTKDFNLDLVSVSKKDSGASPRITSISLCTPGCKTGALMGCNMKTATC

HCSIHVSKIEGRGQSLKTKVAAAVEAAKTVGKGDGTTGTSDKGGGQGTP

APAPGDIGKDKGDEGSQPSSGGNIPTNPATTTSTSTDDTTDRNGQLTSG

KGALPKTGETTERPAFGFLGVIVVILMGVLGL
179 amino acids pTB5-tr2
Immediately upstream LPKTG sequence
MSTKDFNLDLVSVSKKDSGASPRITSISLCTPGCKTGALMGCNMKTATC

HCSIHVSKIEGRGQSLKTKVAAAVEAAKTVGKGDGTTGTSDKGGGQGTP

APAPGDIGKDKGDEGSQPSSGGNIPTNPATTTSTSTDDTTDRNGQLTSG

KGA
150 amino acids pTB5-tr3
MSTKDFNLDLVSVSKKDSGASPRITSISLCTPGCKTGALMGCNMKTATC

HCSIHVSKIEGRGQSLKTKVAAAVEAAKTVGKGDGTTGTSDKGGGQGTP

```
APAPGDI
105 amino acids pTB5-tr4
MSTKDFNLDLVSVSKKDSGASPRITSISLCTPGCKTGALMGCNMKTATC HCSIHVSKIEGRGQSLKTKVAAAVEAAKTVGKGDGT
85 amino acids
```

Truncated prenisin anchor TB5 variants were expressed. Peptides in the supernatant were precipitated by TCA precipitation and analysed on SDS PAGE.

Results

Antimicrobial Activity

With truncated variants 2, 3, 4 there seems some effect of the supernatant on the growth of the indicator strain MG1363. This indicates that the peptides are modified and released. With these variants there is also some autoinduction present. No inhibition of growth was found with truncated variant 1. This variant contains the transmembrane membrane part and likely remains at least largely associated with the cell.

On SDS PAA gel, one band is observed which migrates identically for all truncated variants. This peptide band seemed to migrate at the molecular weight of nisin A single peptide band was observed in TCA precipitated supernatant as shown in the Coomassie stained SDS-PAA gel. The overlay analysis demonstrated that this peptide inhibited the growth of the indicator strain. Production of this nisin band was higher when the truncated protein was shorter (Data not shown).

Conclusion:

The anchoring part of TB5 stabilizes the TB5 prenisin anchor fusion protein. In the absence of this part degradation occurs and active nisin is liberated.

Example 5

Surface Display of Cyclic Angiotensin Analogs

Objective:

Demonstrating surface display and modification of angiotensin-(1-7). Surface display was evaluated with a whole cell ELISA. Modification of angiotensin-(1-7) was demonstrated with antibodies raised specifically against cyclic angiotensin-(1-7) with keyhole limpet hemocyanin (KLH) as a carrier protein.

Materials and Methods

The coding sequence of angiotensin(1-7) (DRVSHIC) was translationally fused to the nisin-leader peptide sequence, separated by a Factor Xa recognition sequence (IEGR). This resulted in angiotensin-(1-7) surface display vector pTB2 (FIG. 1A). *L. lactis* NZ9000, and NZ9000 (pIL3BTC) cells with pTB2 were grown with and without induction of TB2. Cells from these production cultures were collected, washed with PBS, and finally resuspended in PBS until $OD_{600} \approx 20\text{-}30$. The whole cell ELISA was performed as described in Example 2.

In addition, production of the leader peptide angiotensin-(1-7)-anchor protein was analyzed by SDS-PAGE, and Western blotting using anti cyclic-angiotensin-(1-7) antibodies.

Results

Figure 5A:
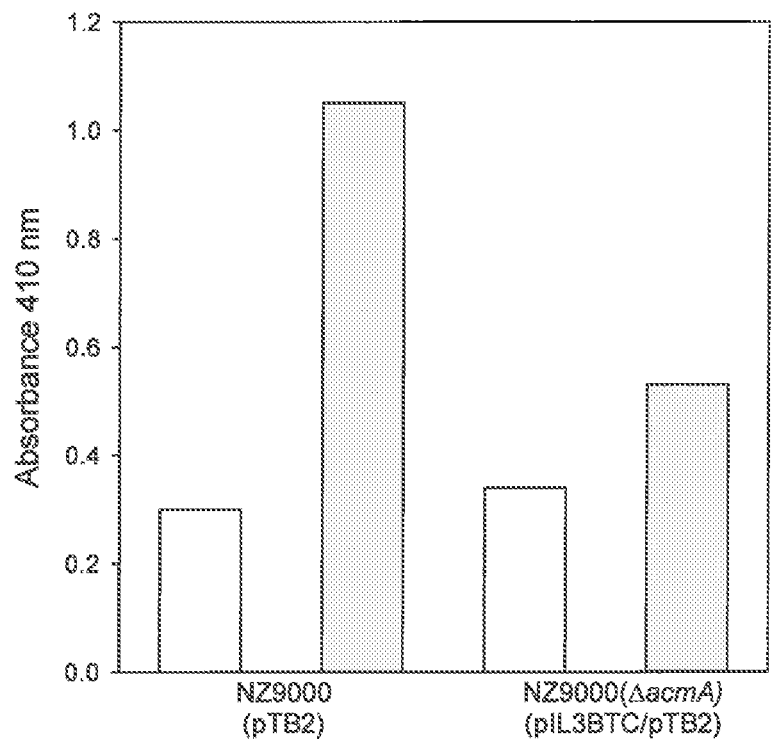

Cells from induced cultures generated a positive color response for the modified TB2 as well as for the non-modified TB2 (FIG. 5A). This demonstrated that the leader peptide was accessible from the outside, and thus angiotensin-(1-7) was displayed on the lactococcal cell surface.

Figure 5B:
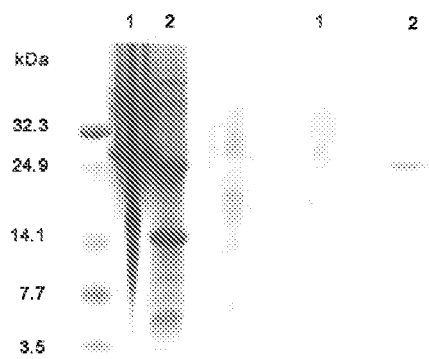
Figure 5D:
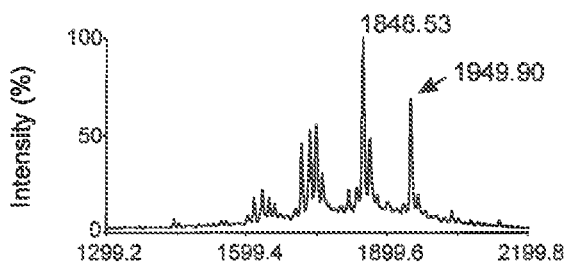
Figure 5D:
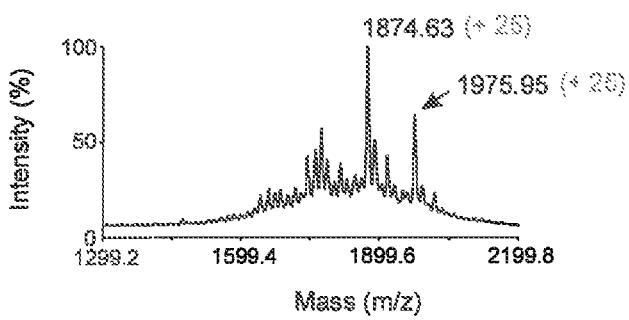
Figure 5D:
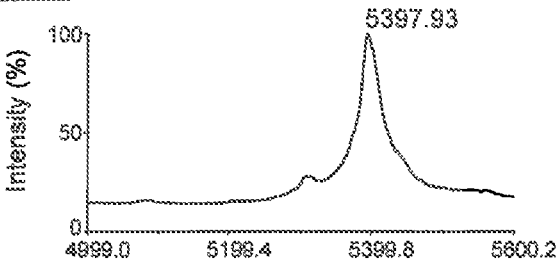
Figure 5D:
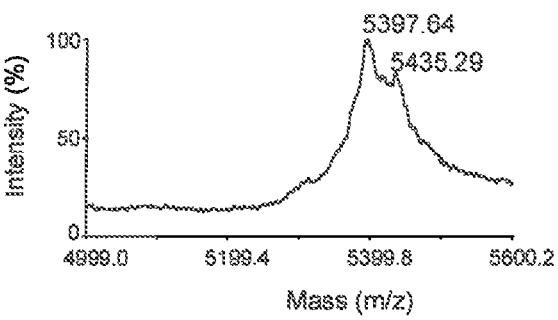

SDS-PAGE analysis of cell extracts from TB2 displaying *L. lactis* cells clearly showed a protein band migrating around the 24.9 kDa marker band. Western analysis with anti cyclic-angiotensin-(1-7) antbodies identified this protein band as TB2 (FIG. 5B). The used cyclic-angiotensin-(1-7) antibodies were raised in mice against purified cyclic-angiotensin(1-7) with KLH as a carrier protein. In standard ELISA these antibodies were at least $10^4$-fold more specific for the cyclic-angiotensin-(1-7) than for its linear counterpart. Thus, anti cyclic-angiotensin(1-7) antibodies recognized specifically the modified angiotensin-(1-7). The Western blot clearly showed an immunoreactive signal of the anti cyclic-angiotensin-(1-7) antibodies with modified TB2 (FIG. 5B, lane 2), whereas no signal was found with non-modified TB2 (FIG. 5B, lane 1)). This indicated that the displayed angiotensin-(1-7) was modified by NisB and NisC. Maldi TOF analysis shows that the displayed angiotensin-(1-7) is dehydrated (FIG. 5C) and cyclized (FIG. 5D).

Example 6

Mass Spectrometry Analysis of Modified TB1

Objective:

Demonstrating modification of nisin within TB1 by MALDI-TOF analysis

Materials and Methods

Lactococcal surface display vector pTB1 was constructed to facilitate purification and analysis. Plasmid pTB1 encoded a human rhinovirus 3C protease recognition sequence (PreScission protease, GE Healthcare) to release the N-terminal part encoding leader peptide, nisin, and Strep tag II from the lactococcal cell surface. The Strep tag II sequence was included for purification purposes.

*L. lactis* NZ9000 cells displaying TB1 were extracted with 16% trichloroacetic acid for 30 min on ice. Cells were washed twice with 1 ml aceton, dried in speed vac, and resuspended in 0.25 ml 10 mM Tris-HCl pH 8.0, 1 mM EDTA, 1 mg lysozyme, and 0.1 mg mutanolysin. Cell wall digestion was performed at 37° C. for 1 hr. Cells were collected by centrifugation, washed twice with PBS. The cells were resuspended in 1 ml PreScission protease cleavage buffer (50 mM Tris-HCl, pH 7.0, 150 mM NaCl, 1 mM EDTA, 1 mM DTT) with 40 U PreScission protease (GE Healthcare) and incubated at 4° C. for 24-48 hr under rotation.

After protease digestion the supernatant was collected and the strep-tagged N-terminal part of TB1 peptide was purified using Strep-tactin spin column purification kit (IBA, GmbH) according instructions of the manufacturer. Peptides in the eluate were precipitated with 10% TCA and dissolved in water Mass spectra were recorded with a Voyager DE PRO matrix-assisted laser desorption ionization-time of flight (MALDI-TOF) mass spectrometer in the linear mode.

Results

The purified N-terminal part of TB1 was analyzed by MALDI-TOF (FIG. 6). The spectrum in FIG. 6A shows a mass peak around 7975 Da, which corresponded to the full-length N-terminal TB1 part schematically indicated in the figure. This peak disappeared when the sample was treated with trypsin, while a mass peak around 3389 Da emerged (FIG. 6B). The latter mass peak corresponded to the nisin part of TB1. The fact that this fragment appeared already demonstrates modification of nisin since it is protected against trypsin digestion. FIG. 6C shows a more detailed analysis of the nisin mass peak from TB1. At least the seven- and sixfold dehydration mass peaks are clearly present in the spectrum TB1 nisin. Compared to secreted nisin the 8-fold dehydration peak is lacking (FIG. 6D).

Conclusion:

These data demonstrate that nisin within TB1 is modified and contained at least 7 dehydrations.

Example 7

Objective

Selection of Streptavidin Binding Peptide by Display and Screening

Materials and Methods

To demonstrate the proof of principle of display and screening, experiments were performed aiming at the selection of a streptavidin binding peptide out of a library containing ISXXXCNMKTATCHCSIHVSK, in which X is any amino acid. Three randomized amino acids were flanked by a serine and a cysteine which allows enzyme-catalyzed dehydration of the serine and cyclase-catalyzed coupling of the resulting dehydroalanine to the cysteine. The use of NNS codons for library construction allows all possible amino acids at each position between the serine and the cysteine, yielding a library with a theoretical protein diversity of 8000 variants. The estimated library size was about 11000 independent clones. The construct encoding this lactococcal thioether peptide display library was termed pRND-X3 (FIG. 1A). We screened the library for streptavidin binders. After two rounds of magnetic selection (MACS) using streptavidin-coated magnetic beads selected bacteria were plated for analysis.

Results

Analysis of the selected clones exclusively yielded one single sequence: S-MNV-C (pRND-X3-1), which as a disulfide-bridged motif was known but not as a thioether-cyclized motif. The absence of sequence variation within the analyzed selected peptides is likely due to the conformational constraints imposed by the thioether bridge combined with the requirements for streptavidin binding. Lactococcal cells displaying this MNV-containing polypeptide generated a positive color response in a whole cell ELISA, thus proving binding to streptavidin. Furthermore, binding was abolished in the presence of biotin, demonstrating the specificity for the biotin binding site (FIG. 7). Analyses with Maldi TOF revealed that CDAP did not add to the MNV-containing peptide, which precludes the presence of an unmodified cysteine thus proving that a thioether bridge was present (FIG. 8). Hence, a thioether-bridged peptide with affinity for streptavidin can be readily selected from the lactococcal thioether peptide display library.

CONCLUSION the lactococcal library of cell-surface displayed thioether-bridged peptides can be successfully screened for a specific ligand.

INCORPORATION OF SEQUENCE LISTING

Incorporated herein by reference in its entirety is the Sequence Listing for the application. The Sequence Listing is disclosed on a computer-readable ASCII text file entitled "Sequence_listing_294-418PCTUS.txt," created on Mar. 19, 2013. The sequence.txt file is 14 kilobyte in size.

The invention claimed is:

1. A Gram-positive host cell capable of post-translationally modifying a polypeptide of interest to a dehydroresidue or thioether bridge containing polypeptide, wherein the host cell comprises an expression vector comprising a nucleic acid construct encoding a fusion peptide comprising, from the N-terminus to the C-terminus, at least the following sequential elements:

(a) an N-terminal lantibiotic leader sequence that can be recognized by a lantiobiotic dehydratase and a lantibiotic cyclase;

(b) an amino acid sequence of interest to be post-translationally modified to a dehydroresidue- or thioether-bridge containing polypeptide;

(c) a hydrophilic cell-wall spanning domain;

(d) a sortase recognition motif;

(e) a hydrophobic membrane spanning domain; and (f) a C-terminal charged membrane anchoring domain and wherein the host cell is a lactic bacterium that contains lantibiotic biosynthesis enzymes and a lantiobiotic transporter which exports the post-translationally modified polypeptide out of the host cell.

2. A host cell according to claim 1, wherein said lantibiotic leader sequence is a nisin leader sequence.

3. A host cell according to claim 1, wherein said cell wall-spanning domain is derived from the cell wall-spanning domain of a multi-domain, cell-envelope proteinase of a lactic acid bacterium.

4. A host cell according to claim 3, wherein said cell-wall spanning domain comprises the amino acid sequence of a cell wall-spanning domain of prtH of *Lactobacillus helveticus*, prtP of *Lactococcus lactis*, scpA of *Streptococcus pyogenes* or esp of *Streptococcus agalactiae*, or a functional analog or fragment thereof.

5. A host cell according to claim 1, wherein said sortase-recognition motif comprises the amino acid sequence LPXTG (SEQ ID NO:27) wherein X may be the amino acid D, E, A, N, Q, or K.

6. A host cell according to claim 1, wherein said hydrophobic membrane spanning domain has a length of 20 to 30 amino acids.

7. A host cell according to claim 1, wherein said charged membrane anchoring domain has a length of at least four amino acid residues.

8. A host cell according to claim 1, wherein the fusion peptide further comprises, between elements (a) and (b), and/or between elements (b) and (c), at least one proteolytic cleavage site.

9. A host cell according to claim 8, comprising a factor Xa protease recognition site between elements (a) and (b).

10. A host cell according to claim 8 comprising a human rhinovirus 3C protease recognition site.

11. A host cell according to claim 1, wherein the amino acid sequence of interest is a therapeutically relevant peptide.

12. A host cell according to claim 1, wherein the lactic acid bacterium is selected from *Lactococcus lactis, Bacillus subtilis, Streptococcus pyogenes, Staphylococcus epidermis, Staphylococcus gallinarium, Staphylococcus aureus, Streptococcus mutans, Staphylococcus warneri, Streptococcus salivarius, Lactobacillus sakei, Lactobacillus plantarum, Carnobacterium piscicola, Enterococcus faecalis, Micro coccus varians, Streptomyces* OH-4156, *Streptomyces cinnamoneus, Streptomyces griseoluteus, Butyrivibrio fibriosolvens, Streptoverticillium hachijoense, Actinoplanes linguriae, Ruminococcus gnavus, Streptococcus macedonicus, Streptococcus bovis*.

13. A library of host cells comprising a plurality of host cells according to claim 1, wherein each member of said library displays at its cell surface a different dehydroresidue- or thioether-bridge containing polypeptide.

14. A method for identifying a dehydroresidue- or thioether-containing polypeptide capable of binding to a target entity of interest, which method comprises the steps of:

(a) providing a library according to claim 13;

(b) selecting from the library at least one host cell displaying a dehydroresidue- or thioether-bridge containing polypeptide capable of binding to the target entity of interest; and (c) identifying the polypeptide sequence displayed on said at least one selected host cell.

15. The host cell according to claim 5, wherein said sortase-recognition motif consists of LPKTG.

16. The host cell according to claim 7, wherein at least 50% of the residues of the membrane anchoring domain are positively charged amino acids.

17. The host cell according to claim 16, wherein said positively charged amino acids comprise Lys and/or Arg residues.

18. The host cell according to claim 9, wherein the factor Xa protease recognition site comprises the amino acid sequence IEGR (SEQ ID NO:17).

19. The host cell according to claim 10, wherein the human rhinovirus 3C protease recognition site comprises the amino acid sequence EALFQGP (SEQ ID NO:28).

20. The host cell according to claim 11, wherein the therapeutically relevant peptide is selected from the group consisting of a hormone, an enzyme inhibitor, an enzyme activator, a receptor ligand, an inhibitory peptide, a lantibiotic protein, and a viral protein.

\* \* \* \* \*